(12) United States Patent
Deisseroth et al.

(10) Patent No.: US 10,035,027 B2
(45) Date of Patent: Jul. 31, 2018

(54) DEVICE AND METHOD FOR ULTRASONIC NEUROMODULATION VIA STEREOTACTIC FRAME BASED TECHNIQUE

(75) Inventors: Karl Deisseroth, Palo Alto, CA (US); M. Bret Schneider, Portola Valley, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 593 days.

(21) Appl. No.: 12/263,026

(22) Filed: Oct. 31, 2008

(65) Prior Publication Data

US 2009/0112133 A1      Apr. 30, 2009

Related U.S. Application Data

(60) Provisional application No. 60/984,225, filed on Oct. 31, 2007.

(51) Int. Cl.
*A61N 7/02* (2006.01)
*A61N 7/00* (2006.01)

(52) U.S. Cl.
CPC ........ *A61N 7/00* (2013.01); *A61N 2007/0026* (2013.01); *A61N 2007/0078* (2013.01); *A61N 2007/0095* (2013.01); *A61N 2007/027* (2013.01)

(58) Field of Classification Search
CPC .... A61N 2007/0026; A61N 2007/0027; A61N 2007/0078; A61N 2007/0086–2007/0095; A61N 2007/0021–2007/003

(Continued)

(56) References Cited

U.S. PATENT DOCUMENTS 2,968,302 A   1/1961  Fry et al.
3,131,690 A   5/1964  Innis et al.
(Continued)

FOREIGN PATENT DOCUMENTS

CN   1079464 A   12/1993
CN   1558222 A   12/2004
(Continued)

OTHER PUBLICATIONS

TimothyWagner, Noninvasive Human Brain Stimulation, Apr. 2007, Annu. Rev. Biomed. Eng. 2007. 9:19.1-19.39.*
(Continued)

*Primary Examiner* — Serkan Akar
(74) *Attorney, Agent, or Firm* — Bozicevic, Field & Francis LLP; Paula A. Borden; Rudy J. Ng

(57) ABSTRACT

One embodiment involves modifying neural transmission patterns between neural structures and/or neural regions in a noninvasive manner. In a related exemplary method, sound waves are directed toward a first targeted neural structure and characteristics of the sound waves are controlled at the first target neural structure with respect to characteristics of sound waves at the second target neural structure. In response, neural transmission patterns modified to produce the intended effect (e.g., long-term potentiation and long-term depression of the neural transmission patterns). In a related embodiment, a transducer produces the sound for stimulating the first neural structure and the second neural structure, and an electronically-based control circuit is used to control characteristics of the sound waves as described above to modify the neural transmission patterns between the first and second neural structures.

27 Claims, 4 Drawing Sheets

(58) Field of Classification Search
USPC .................. 601/1, 2, 3, 4; 606/27; 29/594
See application file for complete search history.

(56) References Cited

U.S. PATENT DOCUMENTS

| | | | |
|---|---|---|---|
| 3,499,437 A | 3/1970 | Balamuth | |
| 3,567,847 A | 3/1971 | Price | |
| 4,343,301 A | 8/1982 | Indech | |
| 4,559,951 A | 12/1985 | Dahl et al. | |
| 4,616,231 A | 10/1986 | Autrey et al. | |
| 4,865,042 A | 9/1989 | Umemura et al. | |
| 4,879,284 A | 11/1989 | Lang et al. | |
| 5,032,123 A | 7/1991 | Katz et al. | |
| 5,041,224 A | 8/1991 | Ohyama et al. | |
| 5,082,670 A | 1/1992 | Gage et al. | |
| 5,249,575 A | 10/1993 | Di Mino et al. | |
| 5,267,152 A | 11/1993 | Yang et al. | |
| 5,290,280 A | 3/1994 | Daikuzono et al. | |
| 5,330,515 A | 7/1994 | Rutecki et al. | |
| 5,382,516 A | 1/1995 | Bush | |
| 5,411,540 A | 5/1995 | Edell et al. | |
| 5,445,608 A | 8/1995 | Chen et al. | |
| 5,460,950 A | 10/1995 | Barr et al. | |
| 5,460,954 A | 10/1995 | Lee et al. | |
| 5,470,307 A | 11/1995 | Lindall | |
| 5,495,541 A | 2/1996 | Murray et al. | |
| 5,520,188 A | 5/1996 | Hennige et al. | |
| 5,527,695 A | 6/1996 | Hodges et al. | |
| 5,550,316 A | 8/1996 | Mintz | |
| 5,641,650 A | 6/1997 | Turner et al. | |
| 5,703,985 A | 12/1997 | Owyang et al. | |
| 5,722,426 A | 3/1998 | Kolff | |
| 5,738,625 A * | 4/1998 | Gluck | 600/9 |
| 5,739,273 A | 4/1998 | Engelman et al. | |
| 5,741,316 A | 4/1998 | Chen et al. | |
| 5,755,750 A | 5/1998 | Petruska et al. | |
| 5,756,351 A | 5/1998 | Isacoff et al. | |
| 5,782,896 A | 7/1998 | Chen et al. | |
| 5,795,581 A | 8/1998 | Segalman et al. | |
| 5,807,285 A | 9/1998 | Vaitekunas et al. | |
| 5,816,256 A | 10/1998 | Kissinger et al. | |
| 5,836,941 A | 11/1998 | Yoshihara et al. | |
| 5,898,058 A | 4/1999 | Nichols | |
| 5,939,320 A | 8/1999 | Littman et al. | |
| 6,056,738 A | 5/2000 | Marchitto et al. | |
| 6,057,114 A | 5/2000 | Akong | |
| 6,108,081 A | 8/2000 | Holtom et al. | |
| 6,134,474 A | 10/2000 | Fischell et al. | |
| 6,161,045 A | 12/2000 | Fischell et al. | |
| 6,180,613 B1 | 1/2001 | Kaplitt et al. | |
| 6,253,109 B1 | 6/2001 | Gielen | |
| 6,303,362 B1 | 10/2001 | Kay et al. | |
| 6,334,846 B1 | 1/2002 | Ishibashi et al. | |
| 6,336,904 B1 | 1/2002 | Nikolchev | |
| 6,346,101 B1 | 2/2002 | Alfano et al. | |
| 6,364,831 B1 | 4/2002 | Crowley | |
| 6,377,842 B1 | 4/2002 | Pogue et al. | |
| 6,436,708 B1 | 8/2002 | Leone et al. | |
| 6,473,639 B1 | 10/2002 | Fischell et al. | |
| 6,480,743 B1 | 11/2002 | Kirkpatrick et al. | |
| 6,489,115 B2 | 12/2002 | Lahue et al. | |
| 6,497,872 B1 | 12/2002 | Weiss et al. | |
| 6,506,154 B1 | 1/2003 | Ezion | |
| 6,536,440 B1 | 3/2003 | Dawson | |
| 6,551,346 B2 | 4/2003 | Crossley | |
| 6,567,690 B2 | 5/2003 | Giller et al. | |
| 6,597,954 B1 | 7/2003 | Pless et al. | |
| 6,609,020 B2 | 8/2003 | Gill | |
| 6,615,080 B1 | 9/2003 | Unsworth et al. | |
| 6,631,283 B2 | 10/2003 | Storrie et al. | |
| 6,632,672 B2 | 10/2003 | Calos | |
| 6,647,296 B2 | 11/2003 | Fischell et al. | |
| 6,685,656 B1 | 2/2004 | Duarte et al. | |
| 6,686,193 B2 | 2/2004 | Maher et al. | |
| 6,721,603 B2 | 4/2004 | Zabara et al. | |
| 6,729,337 B2 | 5/2004 | Dawson | |
| 6,780,490 B1 | 8/2004 | Tanaka et al. | |
| 6,790,652 B1 | 9/2004 | Terry et al. | |
| 6,790,657 B1 | 9/2004 | Arya | |
| 6,805,129 B1 | 10/2004 | Pless | |
| 6,808,873 B2 | 10/2004 | Murphy et al. | |
| 6,810,285 B2 | 10/2004 | Pless et al. | |
| 6,889,085 B2 | 5/2005 | Dawson | |
| 6,918,872 B2 | 7/2005 | Yokoi | |
| 6,921,413 B2 | 7/2005 | Mahadevan-Jansen et al. | |
| 6,969,449 B2 | 11/2005 | Maher et al. | |
| 6,974,448 B2 | 12/2005 | Petersen | |
| 7,045,344 B2 | 5/2006 | Kay et al. | |
| 7,091,500 B2 | 8/2006 | Schnitzer | |
| 7,144,733 B2 | 12/2006 | Miesenbock et al. | |
| 7,175,596 B2 | 2/2007 | Vitek et al. | |
| 7,191,018 B2 | 3/2007 | Gielen et al. | |
| 7,211,054 B1 | 5/2007 | Francis et al. | |
| 7,220,240 B2 | 5/2007 | Struys et al. | |
| 7,298,143 B2 | 11/2007 | Jaermann et al. | |
| 7,313,442 B2 * | 12/2007 | Velasco et al. | 607/45 |
| 7,603,174 B2 * | 10/2009 | De Ridder | 607/55 |
| 7,610,100 B2 | 10/2009 | Jaax et al. | |
| 7,613,520 B2 * | 11/2009 | De Ridder | 607/55 |
| 7,686,839 B2 | 3/2010 | Parker | |
| 7,699,778 B2 * | 4/2010 | Adam | 600/439 |
| 7,824,869 B2 | 11/2010 | Hegemann et al. | |
| 7,883,536 B1 | 2/2011 | Bendett | |
| 7,988,688 B2 | 8/2011 | Webb et al. | |
| 8,386,312 B2 | 2/2013 | Pradeep et al. | |
| 8,398,692 B2 | 3/2013 | Deisseroth et al. | |
| 8,696,722 B2 | 4/2014 | Deisseroth et al. | |
| 8,815,582 B2 | 8/2014 | Deisseroth et al. | |
| 8,906,360 B2 | 12/2014 | Deisseroth et al. | |
| 8,926,959 B2 | 1/2015 | Deisseroth et al. | |
| 9,057,734 B2 | 6/2015 | Cohen | |
| 9,079,940 B2 | 7/2015 | Deisseroth et al. | |
| 9,175,095 B2 | 11/2015 | Deisseroth et al. | |
| 9,458,208 B2 | 10/2016 | Deisseroth et al. | |
| 9,522,288 B2 | 12/2016 | Deisseroth et al. | |
| 9,604,073 B2 | 3/2017 | Deisseroth et al. | |
| 2001/0023346 A1 | 9/2001 | Loeb | |
| 2002/0094516 A1 | 7/2002 | Calos et al. | |
| 2002/0155173 A1 | 10/2002 | Chopp et al. | |
| 2002/0164577 A1 | 11/2002 | Tsien et al. | |
| 2002/0190922 A1 | 12/2002 | Tsao | |
| 2002/0193327 A1 | 12/2002 | Nemerow et al. | |
| 2003/0009103 A1 | 1/2003 | Yuste et al. | |
| 2003/0026784 A1 | 2/2003 | Koch et al. | |
| 2003/0040080 A1 | 2/2003 | Miesenbock et al. | |
| 2003/0050258 A1 | 3/2003 | Calos | |
| 2003/0082809 A1 | 5/2003 | Quail et al. | |
| 2003/0088060 A1 | 5/2003 | Benjamin et al. | |
| 2003/0097122 A1 | 5/2003 | Ganz et al. | |
| 2003/0104512 A1 | 6/2003 | Freeman et al. | |
| 2003/0125719 A1 | 7/2003 | Furnish | |
| 2003/0144650 A1 | 7/2003 | Smith | |
| 2003/0204135 A1 * | 10/2003 | Bystritsky | 600/407 |
| 2003/0216721 A1 * | 11/2003 | Diederich et al. | 606/28 |
| 2003/0232339 A1 | 12/2003 | Shu et al. | |
| 2004/0013645 A1 | 1/2004 | Monahan et al. | |
| 2004/0015211 A1 | 1/2004 | Nurmikko et al. | |
| 2004/0023203 A1 | 2/2004 | Miesenbock et al. | |
| 2004/0034882 A1 | 2/2004 | Vale et al. | |
| 2004/0039312 A1 * | 2/2004 | Hillstead et al. | 601/2 |
| 2004/0049134 A1 * | 3/2004 | Tosaya | A61H 23/0236 601/2 |
| 2004/0068202 A1 | 4/2004 | Hansson et al. | |
| 2004/0073278 A1 | 4/2004 | Pachys | |
| 2004/0076613 A1 | 4/2004 | Mazarakis et al. | |
| 2004/0122475 A1 | 6/2004 | Myrick et al. | |
| 2004/0203152 A1 | 10/2004 | Calos | |
| 2004/0216177 A1 | 10/2004 | Jordan et al. | |
| 2004/0267118 A1 * | 12/2004 | Dawson | A61N 7/00 600/437 |
| 2005/0020945 A1 * | 1/2005 | Tosaya | A61H 23/0236 601/2 |
| 2005/0058987 A1 | 3/2005 | Shi et al. | |
| 2005/0088177 A1 | 4/2005 | Schreck et al. | |

(56) References Cited

U.S. PATENT DOCUMENTS

| | | | |
|---|---|---|---|
| 2005/0107753 A1 | 5/2005 | Rezai et al. | |
| 2005/0112759 A1 | 5/2005 | Radisic et al. | |
| 2005/0119315 A1 | 6/2005 | Fedida et al. | |
| 2005/0124897 A1* | 6/2005 | Chopra | 600/459 |
| 2005/0143295 A1 | 6/2005 | Walker et al. | |
| 2005/0143790 A1 | 6/2005 | Kipke et al. | |
| 2005/0153885 A1* | 7/2005 | Yun et al. | 514/12 |
| 2005/0197679 A1* | 9/2005 | Dawson | 607/54 |
| 2005/0202398 A1 | 9/2005 | Hegemann et al. | |
| 2005/0215764 A1* | 9/2005 | Tuszynski et al. | 530/358 |
| 2005/0240127 A1* | 10/2005 | Seip et al. | 601/2 |
| 2005/0267011 A1 | 12/2005 | Deisseroth et al. | |
| 2005/0267454 A1* | 12/2005 | Hissong et al. | 606/27 |
| 2005/0279354 A1 | 12/2005 | Deutsch et al. | |
| 2006/0025756 A1* | 2/2006 | Francischelli et al. | 606/27 |
| 2006/0034943 A1* | 2/2006 | Tuszynski | 424/649 |
| 2006/0057192 A1 | 3/2006 | Kane | |
| 2006/0057614 A1 | 3/2006 | Heintz | |
| 2006/0058671 A1* | 3/2006 | Vitek et al. | 600/447 |
| 2006/0058678 A1* | 3/2006 | Vitek et al. | 600/459 |
| 2006/0100679 A1 | 5/2006 | DiMauro et al. | |
| 2006/0106543 A1 | 5/2006 | Deco et al. | |
| 2006/0155348 A1 | 7/2006 | De Charms | |
| 2006/0161227 A1 | 7/2006 | Walsh et al. | |
| 2006/0167500 A1* | 7/2006 | Towe | A61N 1/32 607/3 |
| 2006/0179501 A1 | 8/2006 | Chan et al. | |
| 2006/0184069 A1 | 8/2006 | Vaitekunas | |
| 2006/0190044 A1 | 8/2006 | Libbus et al. | |
| 2006/0206172 A1 | 9/2006 | DiMauro et al. | |
| 2006/0216689 A1 | 9/2006 | Maher et al. | |
| 2006/0236525 A1* | 10/2006 | Sliwa et al. | 29/594 |
| 2006/0241697 A1 | 10/2006 | Libbus et al. | |
| 2006/0253177 A1 | 11/2006 | Taboada et al. | |
| 2006/0271024 A1 | 11/2006 | Gertner et al. | |
| 2007/0027443 A1 | 2/2007 | Rose et al. | |
| 2007/0031924 A1 | 2/2007 | Li et al. | |
| 2007/0053996 A1 | 3/2007 | Boyden et al. | |
| 2007/0054319 A1 | 3/2007 | Boyden et al. | |
| 2007/0060915 A1 | 3/2007 | Kucklick | |
| 2007/0060984 A1 | 3/2007 | Webb et al. | |
| 2007/0135875 A1* | 6/2007 | Demarais et al. | 607/96 |
| 2007/0156180 A1 | 7/2007 | Jaax et al. | |
| 2007/0191906 A1* | 8/2007 | Iyer et al. | 607/45 |
| 2007/0196838 A1 | 8/2007 | Chesnut et al. | |
| 2007/0197918 A1* | 8/2007 | Vitek et al. | 600/459 |
| 2007/0219600 A1 | 9/2007 | Gertner et al. | |
| 2007/0239080 A1* | 10/2007 | Schaden et al. | 601/4 |
| 2007/0239210 A1* | 10/2007 | Libbus et al. | 607/2 |
| 2007/0253995 A1 | 11/2007 | Hildebrand | |
| 2007/0260295 A1 | 11/2007 | Chen et al. | |
| 2007/0261127 A1 | 11/2007 | Boyden et al. | |
| 2007/0282404 A1 | 12/2007 | Cottrell et al. | |
| 2007/0295978 A1 | 12/2007 | Coushaine et al. | |
| 2008/0020465 A1 | 1/2008 | Padidam | |
| 2008/0027505 A1* | 1/2008 | Levin et al. | 607/46 |
| 2008/0033297 A1* | 2/2008 | Sliwa | 600/439 |
| 2008/0033569 A1* | 2/2008 | Ferren et al. | 623/23.7 |
| 2008/0046053 A1* | 2/2008 | Wagner et al. | 607/116 |
| 2008/0050770 A1 | 2/2008 | Zhang et al. | |
| 2008/0051673 A1 | 2/2008 | Kong et al. | |
| 2008/0060088 A1 | 3/2008 | Shin et al. | |
| 2008/0065158 A1 | 3/2008 | Ben-Ezra et al. | |
| 2008/0065183 A1 | 3/2008 | Whitehurst et al. | |
| 2008/0077200 A1 | 3/2008 | Bendett et al. | |
| 2008/0085265 A1 | 4/2008 | Schneider et al. | |
| 2008/0088258 A1 | 4/2008 | Ng | |
| 2008/0103551 A1 | 5/2008 | Masoud | |
| 2008/0119421 A1* | 5/2008 | Tuszynski et al. | 514/34 |
| 2008/0125836 A1 | 5/2008 | Streeter et al. | |
| 2008/0167261 A1 | 7/2008 | Sclimenti | |
| 2008/0175819 A1 | 7/2008 | Kingsman et al. | |
| 2008/0176076 A1 | 7/2008 | Van Veggel et al. | |
| 2008/0200749 A1* | 8/2008 | Zheng et al. | 600/13 |
| 2008/0221452 A1 | 9/2008 | Njemanze | |
| 2008/0227139 A1* | 9/2008 | Deisseroth et al. | 435/29 |
| 2008/0228244 A1 | 9/2008 | Pakhomov et al. | |
| 2008/0262411 A1 | 10/2008 | Dobak | |
| 2008/0287821 A1 | 11/2008 | Jung et al. | |
| 2008/0290318 A1 | 11/2008 | Van Veggel et al. | |
| 2009/0030930 A1 | 1/2009 | Pradeep et al. | |
| 2009/0054954 A1 | 2/2009 | Foley et al. | |
| 2009/0088680 A1 | 4/2009 | Aravanis et al. | |
| 2009/0093403 A1 | 4/2009 | Zhang et al. | |
| 2009/0099038 A1 | 4/2009 | Deisseroth et al. | |
| 2009/0118800 A1 | 5/2009 | Deisseroth et al. | |
| 2009/0148861 A1 | 6/2009 | Pegan et al. | |
| 2009/0157145 A1 | 6/2009 | Cauller | |
| 2009/0069261 A1 | 10/2009 | Nikolov et al. | |
| 2009/0131837 A1 | 10/2009 | Zhang et al. | |
| 2009/0254134 A1* | 10/2009 | Nikolov et al. | 607/3 |
| 2009/0268511 A1 | 10/2009 | Birge et al. | |
| 2009/0306474 A1 | 12/2009 | Wilson | |
| 2009/0319008 A1 | 12/2009 | Mayer | |
| 2009/0326603 A1 | 12/2009 | Boggs | |
| 2010/0009444 A1 | 1/2010 | Herlitze et al. | |
| 2010/0016783 A1 | 1/2010 | Bourke et al. | |
| 2010/0021982 A1 | 1/2010 | Herlitze | |
| 2010/0145418 A1 | 6/2010 | Zhang et al. | |
| 2010/0146645 A1 | 6/2010 | Vasar et al. | |
| 2010/0190229 A1 | 7/2010 | Zhang et al. | |
| 2010/0209352 A1 | 8/2010 | Hultman et al. | |
| 2010/0234273 A1 | 9/2010 | Boyden et al. | |
| 2011/0021270 A1 | 1/2011 | Vo-Dinh et al. | |
| 2011/0092800 A1 | 4/2011 | Yoo et al. | |
| 2011/0105998 A1 | 5/2011 | Deisseroth et al. | |
| 2011/0112179 A1 | 5/2011 | Deisseroth et al. | |
| 2011/0112463 A1 | 5/2011 | Silver et al. | |
| 2011/0125077 A1 | 5/2011 | Denison et al. | |
| 2011/0125078 A1 | 5/2011 | Denison et al. | |
| 2011/0159562 A1 | 6/2011 | Deisseroth et al. | |
| 2011/0165681 A1 | 7/2011 | Boyden et al. | |
| 2011/0166632 A1 | 7/2011 | Delp et al. | |
| 2011/0172653 A1 | 7/2011 | Deisseroth et al. | |
| 2011/0233046 A1 | 9/2011 | Nikolenko et al. | |
| 2011/0301529 A1 | 12/2011 | Zhang et al. | |
| 2011/0311489 A1 | 12/2011 | Deisseroth et al. | |
| 2012/0093772 A1 | 4/2012 | Horsager et al. | |
| 2012/0121542 A1 | 5/2012 | Chuong et al. | |
| 2012/0253261 A1 | 10/2012 | Poletto et al. | |
| 2013/0030275 A1 | 1/2013 | Seymour et al. | |
| 2013/0144359 A1 | 6/2013 | Kishawi et al. | |
| 2013/0286181 A1 | 10/2013 | Betzig et al. | |
| 2015/0112411 A1 | 4/2015 | Beckman et al. | |

FOREIGN PATENT DOCUMENTS

| | | | |
|---|---|---|---|
| CN | 102076866 A | 5/2011 | |
| CN | 103313752 A | 9/2013 | |
| CN | 103476456 A | 12/2013 | |
| EP | 1197144 | 4/2002 | |
| EP | 1 334 748 | 8/2003 | |
| EP | 1444889 | 8/2004 | |
| EP | 1873566 | 1/2008 | |
| JP | 2006-295350 | 10/1994 | |
| JP | H09505771 A | 6/1997 | |
| JP | 2004534508 | 11/2004 | |
| JP | 2005034073 A | 2/2005 | |
| JP | 2007530027 A | 11/2007 | |
| JP | 2008010422 A | 1/2008 | |
| JP | 2010227537 A | 10/2010 | |
| JP | 2012508581 | 4/2012 | |
| WO | WO 1995/005214 | 2/1995 | |
| WO | WO 1996/032076 | 10/1996 | |
| WO | WO 00/27293 * | 5/2000 | A61B 17/22 |
| WO | WO 2001-025466 | 4/2001 | |
| WO | WO 03/106486 A2 | 2/2003 | |
| WO | WO 2013/016486 | 2/2003 | |
| WO | WO 2003-040323 | 5/2003 | |
| WO | WO 2003/046141 | 6/2003 | |
| WO | WO 2003-84994 | 10/2003 | |
| WO | WO 2003-102156 | 12/2003 | |
| WO | WO 2004/033647 | 4/2004 | |
| WO | WO 2005/074932 | 8/2005 | |

(56) References Cited

FOREIGN PATENT DOCUMENTS

| WO | WO 2005/093429 | 10/2005 |
|---|---|---|
| WO | WO 2006/103678 | 10/2006 |
| WO | WO 2007-024391 | 3/2007 |
| WO | WO 2007-131180 | 11/2007 |
| WO | WO 2008/014382 | 1/2008 |
| WO | WO 2008/086470 | 7/2008 |
| WO | WO 2008/106694 | 9/2008 |
| WO | WO 2009/025819 | 2/2009 |
| WO | WO 2009/072123 | 6/2009 |
| WO | WO2009/119782 | 10/2009 |
| WO | WO 2009-131837 | 10/2009 |
| WO | WO 2009/148946 | 12/2009 |
| WO | WO 2010/006049 | 1/2010 |
| WO | WO 2010/011404 A3 | 1/2010 |
| WO | WO 2010/056970 | 5/2010 |
| WO | WO-2010123993 | 10/2010 |
| WO | WO 2011/005978 | 1/2011 |
| WO | WO 2011/066320 A3 | 6/2011 |
| WO | WO 2011/106783 | 9/2011 |
| WO | WO 2011-116238 A2 | 9/2011 |
| WO | WO 2011/127088 A3 | 10/2011 |
| WO | WO 2012/032103 | 3/2012 |
| WO | WO 2012/061676 | 5/2012 |
| WO | WO2012/061681 | 5/2012 |
| WO | WO2012/061684 | 5/2012 |
| WO | WO2012/061688 | 5/2012 |
| WO | WO2012/061690 | 5/2012 |
| WO | WO 2012/061741 | 5/2012 |
| WO | WO 2012/061744 | 5/2012 |
| WO | 2012/106407 | 8/2012 |
| WO | WO 2012/134704 A2 | 10/2012 |
| WO | WO 2013/003557 | 1/2013 |
| WO | WO 2013/090356 | 6/2013 |
| WO | WO 2013/126521 | 8/2013 |
| WO | WO 2013/126762 | 8/2013 |
| WO | WO 2013/142196 | 9/2013 |
| WO | WO 2014/081449 | 5/2014 |
| WO | WO 2014/117079 | 7/2014 |
| WO | WO 2016/019075 | 2/2016 |

OTHER PUBLICATIONS

Basil et al. Is There Evidence for Effectiveness of Transcranial Magnetic Stimulation in the Treatment of Psychiatric Disorders? Psychiatry 2005 [November].*
Ibbini et al, A Field Conjugation Method for Direct Synthesis of Hyperthermia Phased-Array Heating Patterns, IEEE Transactions on Ultrasonics. Ferroelectrics, and Frequency Control, vol. 36, No. I . Jan. 1989.*
Balint, et al., "The Nitrate Transporting Photochemical Reaction Cycle of the Pharaonis Halorhodopsin", Biophysical Journal, 2004, vol. 86, pp. 1655-1663.
Wang, et al., "Molecular Determinants Differentiating Photocurrent Properties of Two Channelrhodopsins from Chlamydomonas", 2009, The Journal of Biological Chemistry, vol. 284, No. 9, pp. 5685-5696.
Gradinaru, et al., Molecular and Cellular Approaches for Diversifying and Extending Optogenetics, Cell, 2010, vol. 141, No. 1, pp. 154-165.
Gonzalez, et al., "Cell-Based Assays and Instrumentation for Screening Ion-Channel Targets", DDT, 1999, vol. 4, No. 9, pp. 431439.
Natochin, et al. "Probing rhodopsin-transducin interaction using *Drosophila* Rh1-bovine rhodopsin chimeras," Vision Res., 2006, vol. 46, No. 27: pp. 4575-4581.
Peterlin, et al. "Optical probing of neuronal circuits with calcium indicators," PNAS, 2000, vol. 97, No. 7: pp. 3619-3624.
Arenkiel, et al. "In vivo light-induced activation of neural circuitry in transgenic mice expressing Channelrhodopsin-2", Neuron, 2007, 54:205-218.
Milella et al. "Opposite roles of dopamine and orexin in quinpirole-induced excessive drinking: a rat model of psychotic polydipsia" Psychopharmacology, 2010, 211:355-366.

Marin, et al., The Amino Terminus of the Fourth Cytoplasmic Loop of Rhodopsin Modulates Rhodopsin-Transduction Interaction, The Journal of Biological Chemistry, 2000, vol. 275, pp. 1930-1936.
Hikida et al., "Increased sensitivity to cocaine by cholinergic cell ablation in nucleus accumbens", PNAS, Nov. 2001, 98(23): 13351-13354.
Hikida et al., "Acetylcholine enhancement in the nucleus accumbens prevents addictive behaviors of cocaine and morphine", PNAS, May 2003, 100(10):6169-6173.
Kitabatake et al., "Impairment of reward-related learning by cholinergic cell ablation in the striatum", PNAS, Jun. 2003, 100(13):7965-7970.
Tamai, "Progress in Pathogenesis and Therapeutic Research in Retinitis Pigmentosa and Age Related Macular Degeneration", Nippon Ganka Gakkai Zasshi, vol. 108, No. 12, Dec. 2004 (Dec. 2004), pp. 750-769.
Tye, et al. "Optogenetic investigation of neural circuits underlying brain disease in animal models," Nature Reviews Neuroscience (Mar. 2012), 13(4):251-266.
Airan, et al., "Temporally Precise in vivo Control of Intracellular Signaling", 2009, Nature, vol. 458, No. 7241, pp. 1025-1029.
Braun, "Two Light-activated Conductances in the Eye of the Green Alga *Volvox carteri*", 1999, Biophys J., vol. 76, No. 3, pp. 1668-1678.
Cardin, et al. "Driving Fast spiking Cells Induces Gamma Rhythm and Controls Sensory Responses", 2009, Nature, vol. 459, vol. 7247, pp. 663-667.
Deisseroth et al., "Excitation-neurogenesis Coupling in Adult Neural Stem/Progenitor Cells", 2004, Neuron, vol. 42, pp. 535-552.
Ernst, et al. "Photoactivation of Channelrhodopsin", 2008, vol. 283, No. 3, pp. 1637-1643.
Genbank Accession No. DQ094781 (Jan. 15, 2008).
Gradinaru, et al. "ENpHR: a Natronomonas Halorhodopsin Enhanced for Optogenetic Applications", 2008, Brain Cell Biol., vol. 36 (1-4), pp. 129-139.
Herlitze, et al., "New Optical Tools for Controlling Neuronal Activity", 2007, Curr Opin Neurobiol, vol. 17, No. 1, pp. 87-94.
Jekely, "Evolution of Phototaxis", 2009, Phil. Trans. R. Soc. B, vol. 364, pp. 2795-2808.
Johansen, et al., "Optical Activation of Lateral Amygdala Pyramidal Cells Instructs Associative Fear Learning", 2010, PNAS, vol. 107, No. 28, pp. 12692-12697.
Kianianmomeni, et al. "Channelrhodopsins of Volvox carteri are Photochromic Proteins that are Specifically Expressed in Somatic Cells under Control of Light, Temperature, and the Sex Inducer", 2009, Plant Physiology, vol. 151, No. 1, pp. 347-366.
Knopfel, et al. "Optical Probin of Neuronal Circuit Dynamics: Gentically Encoded Versus Classical Fluorescent Sensors", 2006, Trends Neurosci, vol. 29, No. 3, pp. 160-166.
McAllister, "Cellular and Molecular Mechanisms of Dendrite Growth", 2000, Cereb Cortex, vol. 10, No. 10, pp. 963-973.
Pape, et al., "Plastic Synaptic Networks of the Amygdala for the Acquisition, Expression, and Extinction of Conditioned Fear", 2010, Physiol Rev, vol. 90, pp. 419-463.
Rammes, et al., "Synaptic Plasticity in the Basolateral Amygdala in Transgenic Mice Expressing Dominant-Negative cAMP Response Element-binding Protein (CREB) in Forebrain", Eur J. Neurosci, 2000, vol. 12, No. 7, pp. 2534-2546.
Randic, et al. "Long-term Potentiation and Long-term Depression of Primary Afferent Neurotransmission in the Rat Spinal Cord", 1993, Journal of Neuroscience, vol. 13, No. 12, pp. 5228-5241.
Ritter, et al., "Monitoring Light-induced Structural Changes of Channelrhodopsin-2 by UV-Visable and Fourier Transform Infared Spectroscopy", 2008, The Journal of Biological Chemistry, vol. 283, No. 50, pp. 35033-35041.
Sajdyk, et al., "Excitatory Amino Acid Receptors in the Basolateral Amygdala Regulate Anxiety Responses in the Social Interaction Test", Brain Research, 1997, vol. 764, pp. 262-264.
Swanson, "Lights, Opsins, Action! Optogenetics Brings Complex Neuronal Circuits into Sharper Focus", 2009, The Dana Foundation, [URL: http://www.dana.org/news/features/detail.aspx?id=24236], PDF File, pp. 1-3.

(56) References Cited

OTHER PUBLICATIONS

Swiss-Prot_Q2QCJ4, Opsin 1, Oct. 31, 2006, URL: http://www.ncbi.nlm.nig.gov/protein/Q2QCJ4.
"SubName: Full=Channelrhodopsin-1", retrieved from EBI accession No. UNIPROT: B4Y103. Database accession No. B4Y103. Sep. 23, 2008.
Fiala et al., "Optogenetic approaches in neuroscience", Current Biology, Oct. 2010, 20(20): R897-R903.
Gradinaru et al., "Optical deconstruction of parkinsonian neural circuitry", Science, Apr. 2009, 324(5925):354-359.
Liu et al., "Optogenetics 3.0", Cell, Apr. 2010, 141(1):22-24.
Malin et al., "Involvement of the rostral anterior cingulate cortex in consolidation of inhibitory avoidance memory: Interaction with the basolateral amygdala", Neurobiol Learning Mem,2007,87(2):295-302.
Mayford et al., "Control of memory formation through regulated expression of CAMKII Transgene", Science, Dec. 1996, 274:1678-1683.
Schroll et al., "Light-induced activation of distinct modulatory neurons triggers appetitive or aversive learning in *Drosophila* larvae", Current Biology, Sep. 2006, 16(17):1741-1747.
Fox et al., "A gene neuron expression fingerprint of C. elegans embryonic motor neurons", BMC Genomics, 2005, 6(42):1-23.
Nonet, "Visualization of synaptic specializations in live C. elegans with synaptic vesicle protein-GFP fusions", J. Neurosci. Methods, 1999, 89:33-40.
Synapse, Chapter 13, http://michaeldmann.net/mann13.html, downloaded Apr. 2014.
Aebischer, et al. "Long-Term Cross-Species Brain Transplantation of a Polymer-Encapsulated Dopamine-Secreting Cell Line", Experimental Neurology, 1991, vol. 111, pp. 269-275.
Ahmad, et al. "The *Drosophila rhodopsin* cytoplasmic tail domain is required for maintenance of rhabdomere structure." The FASEB Journal, 2007, vol. 21, p. 449-455.
Akirav, et al. "The role of the medial prefrontal cortex-amygdala circuit in stress effects on the extinction of fear", Neural Plasticity, 2007: vol. 2007 Article ID:30873, pp. 1-11.
Ang, et at. "Hippocampal CA1 Circuitry Dynamically Gates Direct Cortical Inputs Preferentially at Theta Frequencies." The Journal of Neurosurgery, 2005, vol. 25, No. 42, pp. 9567-9580.
Araki, et al. "Site-Directed Integration of the cre Gene Mediated by Cre Recombinase Using a Combination of Mutant lox Sites", Nucleic Acids Research, 2002, vol. 30, No. 19, pp. 1-8.
Aravanis, et al. "An optical neural interface: in vivo control of rodent motor cortex with integrated fiberoptic and optogenetic technology," J. Neural. Eng., 2007, vol. 4(3):S143-S156.
Argos, et al. "The integrase family of site-specific recombinases: regional similarities and global diversity", The EMBO Journal, 1986, vol. 5, No. 2, pp. 433-440.
Bamberg et al. "Light-driven proton or chloride pumping by halorhodopsin." Proc. Natl. Academy Science USA, 1993, vol. 90, No. 2, p. 639-643.
Banghart, et al. "Light-activated ion channels for remote control of neuronal firing". Nature Neuroscience, 2004, vol. 7, No. 12 pp. 1381-1386.
Bebbington et al., "The use of vectors based on gene amplification for the expression of cloned genes in mammalian cells in DNA cloning" vol. 3, Academic Press, New York, 1987.
Benabid "Future strategies to restore brain functions," Conference proceedings from Medicine Meets Millennium: World Congress of Medicine and Health, 2000, 6 pages.
Benoist et al. "In vivo sequence requirements of the SV40 early promotor region" Nature (London), 1981, vol. 290(5804): pp. 304-310.
Berges et al., "Transduction of Brain by Herpes Simplex Virus Vectors", Molecular Therapy, 2007, vol. 15, No. 1: pp. 20-29.
Berridge et al., "The Versatility and Universality of Calcium Signaling", Nature Reviews: Molecular Cell Biology, 2000, vol. 1: pp. 11-21.

Bocquet et al. "A prokaryotic proton-gated ion channel from the nicotinic acetylcholine receptor family." Nature Letters, 2007, vol. 445, p. 116-119.
Boyden, et al. "Millisecond-timescale, genetically targeted optical control of neural activity" Nature Neuroscience, 2005, vol. 8, No. 9: pp. 1263-1268.
Bi, et al. "Ectopic Expression of a Microbial-Type Rhodopsin Restores Visual Responses in Mice with Photoreceptor Degeneration", Neuron, 2006, vol. 50, No. 1: pp. 23-33.
Bi, et al. "Synaptic Modifications in Cultured Hippocampal Neurons: Dependence on Spike Timing, Synaptic Strength, and Postsynaptic Cell Type", Journal of Neuroscience, 1998, vol. 18, No. 24: pp. 10464-1 0472.
Blomer et al., "Highly Efficient and Sustained Gene Transfer in Adult Neurons with Lentivirus Vector", Journal of Virology,1997, vol. 71, No. 9: pp. 6641-6649.
Brinton, et al. "Preclinical analyses of the therapeutic potential of allopregnanolone to promote neurogenesis in vitro and in vivo in transgenic mouse model of Alzheimer's disease." Current Alzheimer Research, 2006, vol. 3, No. 1: pp. 11-17.
Brosenitsch et al, "Physiological Patterns of Electrical Stimulation Can Induce Neuronal Gene Expression by Activating N-Type Calcium Channels," Journal of Neuroscience, 2001, vol. 21, No. 8, pp. 2571-2579.
Callaway, et al. "Photostimulation using caged glutamate reveals functional circuitry in living brain slices", Proc. Natl. Acad. Sci. USA., 1993, vol. 90: pp. 7661-7665.
Campagnola et al. "Fiber-coupled light-emitting diode for localized photostimulation of neurons expressing channelrhodopsin-2." Journal of Neuroscience Methods, 2008, vol. 169, Issue 1. Abstract only.
Cenatiempo "Prokaryotic gene expression in vitro: transcription-translation coupled systems", Biochimie, 1986, vol. 68(4): pp. 505-515.
Claudio et al. "Nucleotide and deduced amino acid sequences of Torpedo californica acetylcholine receptor gamma subunit." PNAS USA,1983, vol. 80, p. 1111-1115.
Collingridge et al. "Inhibitory post-synaptic currents in rat hippocampal CA1 neurones." J. Physiol., 1984, vol. 356, pp. 551-564.
Covington, et al. "Antidepressant Effect of Optogenetic Stimulation of the Medial Prefrontal Cortex." Journal of Neuroscience, 2010, vol. 30(48), pp. 16082-16090.
Crouse, et al. "Expression and amplification of engineered mouse dihydrofolate reductase minigenes" Mol. Cell. Biol., 1983, vol. 3(2): pp. 257-266.
Cucchiaro et al., "Phaseolus vulgaris leucoagglutinin (PHA-L): a neuroanatomical tracer for electron microscopic analysis of synaptic circuitry in the cat's dorsal lateral geniculate nucleus" J. Electron. Microsc. Tech., 1990, 15 (4):352-368.
Cucchiaro et al., "Electron-Microsoft Analysis of Synaptic Input from the Perigeniculate Nucleus to A-Lamine of the Lateral Geniculate Nucleus in Cats", The Journal of Comparitive Neurology, 1991, vol. 310, pp. 316-336.
Cui, et al., "Electrochemical deposition and characterization of conducting polymer polypyrrole/PSS on multichannel neural probes," Sensors and Actuators, 2001, vol. 93(1): pp. 8-18.
Date, et al. "Grafting of Encapsulated Dopamine-Secreting Cells in Parkinson's Disease: Long-Term Primate Study", Cell Transplant, 2000, vol. 9, pp. 705-709.
Dalva, et al. "Rearrangements of Synaptic Connections in Visual Cortex Revealed by Laser Photostimulation", Science, 1994,vol. 265, pp. 255-258.
Dederen, et al. "Retrograde neuronal tracing with cholera toxin B subunit: comparison of three different visualization methods", Histochemical Journal, 1994, vol. 26, pp. 856-862.
De Foubert et al. "Fluoxetine-Induced Change in Rat Brain Expression of Brain-Derived Neurotrophic Factor Varies Depending on Length of Treatment," Neuroscience, 2004, vol. 128, pp. 597-604.
Deisseroth et al., "Signaling from Synapse to Nucleus: Postsynaptic CREB Phosphorylation During Multiple Forms of Hippocampal Synaptic Plasticity", Neuron, 1996, vol. 16, pp. 89-101.

(56) References Cited

OTHER PUBLICATIONS

Deisseroth et al., "Translocation of Calmodulin to the Nucleus Supports CREB Phosphorylation in Hippocampal Neurons", Nature, 1998, vol. 392, pp. 198-202.
Deisseroth et al., "Signaling from Synapse to Nucleus: the logic Behind the Mechanisms", Currrent Opinion in Neurobiology, 2003, vol. 13, pp. 354-365.
Deisseroth "Next-generation optical technologies for illuminating genetically targeted brain circuits," The Journal of Neuroscience, 2006, vol. 26, No. 41, pp. 10380-10386.
Denk, W., et al. "Anatomical and functional imaging of neurons using 2-photon laser scanning microscopy", Journal of Neuroscience Methods, 1994, vol. 54, pp. 151-162.
Ditterich, et al. "Microstimulation of visual cortex affects the speed of perceptual decisions", 2003, Nature Neuroscience, vol. 6, No. 8, pp. 891-898.
Dittgen, et al. "Lentivirus-based genetic manipulations of cortical neurons and their optical and electrophysiological monitoring in vivo", PNAS, 2004, vol. 101, No. 52, pp. 18206-18211.
Emerich, et al. "A Novel Approach to Neural Transplantation in Parkinson's Disease: Use of Polymer-Encapsulated Cell Therapy", Neuroscience and Biobehavioral Reviews, 1992, vol. 16, pp. 437-447.
Ensell, et al. "Silicon-based microelectrodes for neurophysiology, micromachined from silicon-on-insulator wafers," Med. Biol. Eng. Comput., 2000, vol. 38, pp. 175-179.
Eisen, "Treatment of amyotrophic lateral sclerosis", Drugs Aging, 1999; vol. 14, No. 3, pp. 173-196.
Evanko "Optical excitation yin and yang" Nature Methods, 2007, 4:384.
Esposito et al. "The integrase family of tyrosine recombinases: evolution of a conserved active site domain", Nucleic Acids Research, 1997, vol. 25, No. 18, pp. 3605-3614.
Fabian et al. "Transneuronal transport of lectins" Brain Research, 1985, vol. 344, pp. 41-48.
Falconer et al. "High-throughput screening for ion channel modulators," Journal of Biomolecular Screening, 2002, vol. 7, No. 5, pp. 460-465.
Farber, et al. "Identification of Presynaptic Neurons by Laser Photostimulation", Science, 1983, vol. 222, pp. 1025-1027.
Feng, et al. "Imaging Neuronal Subsets in Transgenic Mice Expressing Multiple Spectral Variants of GFP", Neuron, 2000, vol. 28, pp. 41-51.
Fisher, J. et al. "Spatiotemporal Activity Patterns During Respiratory Rhythmogenesis in the Rat Ventrolateral Medulla," The Journal of Neurophysiol, 2006, vol. 95, pp. 1982-1991.
Fitzsimons et al., "Promotors and Regulatory Elements that Improve Adeno-Associated Virus Transgene Expression in the Brain", 2002, Methods, vol. 28, pp. 227-236.
Foster, "Bright blue times", Nature, 2005, vol. 433, pp. 698-699.
Gigg, et al. "Glutamatergic hippocampal formation projections to prefrontal cortex in the rat are regulated by GABAergic inhibition and show convergence with glutamatergic projections from the limbic thalamus," Hippocampus, 1994, vol. 4, No. 2, pp. 189-198.
Gilman, et al. "Isolation of sigma-28-specific promoters from *Bacillus subtilis* DNA" Gene, 1984, vol. 32(1-2): pp. 11-20.
Glick et al."Factors affecting the expression of foreign proteins in *Escherichia coli*", Journal of Industrial Microbiology, 1987, vol. 1(5): pp. 277-282.
Goekoop, R. et al. "Cholinergic challenge in Alzheimer patients and mild cognitive impairment differentially affects hippocampal activation-a pharmacological fMRI study." Brain, 2006, vol. 129, pp. 141-157.
Gold, et al. "Representation of a perceptual decision in developing oculomotor commands", Nature, 2000, vol. 404, pp. 390-394.
Gordon, et al. "Regulation of Thy-1 Gene Expression in Transgenic Mice", Cell, 1987, vol. 50, pp. 445-452.
Gorelova et al., "The course of neural projection from the prefrontal cortex to the nucleus accumbens in the rat ", Neuroscience, 1997, vol. 76, No. 3, pp. 689-706.
Gottesman et al."Bacterial regulation: global regulatory networks," Ann. Rev. Genet. , 1984, vol. 18, pp. 415-441.
Greenberg, et al. "Three-year outcomes in deep brain stimulation for highly resistant obsessive-compulsive disorder," Neuropsychopharmacology, 2006, vol. 31, pp. 2384-2393.
Gregory, et al. "Integration site for *Streptomyces* phage φBT1 and development of site-specific integrating vectors", Journal of Bacteriology, 2003, vol. 185, No. 17, pp. 5320-5323.
Groth et al. "Phage integrases: biology and applications," Journal of Molecular Biology, 2004, vol. 335, pp. 667-678.
Groth, et al. "A phage integrase directs efficient site-specific integration in human cells", PNAS, 2000, vol. 97, No. 11, pp. 5995-6000.
Gulick, et al. "Transfection using DEAE-Dextran" Supplement 40, Current Protocols in Molecular Biology, 1997, Supplement 40, 9.2.1-9.2.10.
Gur et al., "A Dissociation Between Brain Activity and Perception: Chromatically Opponent Cortical Neurons Signal Chromatic Flicker that is not Perceived", Vision Research, 1997, vol. 37, No. 4, pp. 377-382.
Hallet et al. "Transposition and site-specific recombination: adapting DNA cut-and-paste mechanisms to a variety of genetic rearrangements," FEMS Microbiology Reviews, 1997, vol. 21, No. 2, pp. 157-178.
Hamer, et al. "Regulation In Vivo of a cloned mammalian gene: cadmium induces the transcription of a mouse metallothionein gene in SV40 vectors," Journal of Molecular Applied Genetics, 1982, vol. 1, No. 4, pp. 273-288.
Hausser, et al. "Tonic Synaptic Inhibition Modulates Neuronal Output Pattern and Spatiotemporal Synaptic Integration", Neuron, 1997, vol. 19, pp. 665-678.
Hegemann et al., "All-trans Retinal Constitutes the Functional Chromophore in *Chlamydomonas* rhodopsin", Biophys. J. , 1991, vol. 60, pp. 1477-1489.
Herry, et al. "Switching on and off fear by distinct neuronal circuits," Nature, 2008, vol. 454, pp. 600-606.
Hildebrandt et al, "Bacteriorhodopsin expressed in *Schizosaccharomyces pombe* pumps protons through the plasma membrane, " PNAS, 1993, vol. 90, pp. 3578-3582.
Hirase, et al. "Multiphoton stimulation of neurons", J Neurobiol, 2002, vol. 51, No. 3: pp. 237-247.
Hodaie, et al., "Chronic Anterior Thalamus Stimulation for Intractable Epilepsy," Epilepsia, 2002, vol. 43, pp. 603-608.
Hoffman et al., "K+ Channel Regulation of Signal Propagation in Dendrites of Hippocampal Pyramidal Neurons", 1997, Nature, vol. 387: pp. 869-874.
Hosokawa, T. et al. "Imaging spatio-temporal patterns of long-term potentiation in mouse hippocampus." Philos. Trans. R. Soc. Lond. B., 2003, vol. 358, pp. 689-693.
International Search Report for International Application No. PCT/US2009/053474, dated Oct. 8, 2009.
Isenberg et al. "Cloning of a Putative Neuronal Nicotinic Aceylcholine Receptor Subunit," Journal of Neurochemistry, 1989, pp. 988-991.
Johnston et al. "Isolation of the yeast regulatory gene GAL4 and analysis of its dosage effects on the galactose/melibiose regulon," PNAS, 1982, vol. 79, pp. 6971-6975.
Kandel, E.R.,et al. "Electrophysiology of Hippocampal Neurons: I. Sequential Invasion and Synaptic Organization," J Neurophysiol, 1961, vol. 24, pp. 225-242.
Kandel, E.R.,et al. "Electrophysiology of Hippocampal Neurons: Ii. After-Potentials and Repetitive Firing", J Neurophysiol., 1961, vol. 24, pp. 243-259.
Karreman et al. "On the use of double FLP recognition targets (FRTs) in the LTR of retroviruses for the construction of high producer cell lines" , Nucleic Acids Research, 1996, vol. 24, No. 9: pp. 1616-1624.
Katz, et al. "Scanning laser photostimulation: a new approach for analyzing brain circuits," Journal of Neuroscience Methods, 1994, vol. 54, pp. 205-218.

(56) References Cited

OTHER PUBLICATIONS

Khodakaramian, et al. "Expression of Cre Recombinase during Transient Phage Infection Permits Efficient Marker Removal in *Streptomyces*," Nucleic Acids Research, 2006, vol. 34, No. 3:e20, pp. 1-5.

Khossravani et al., "Voltage-Gated Calcium Channels and Idiopathic Generalized Epilepsies", Physiol. Rev., 2006, vol. 86: pp. 941-966.

Kim et al., "Light-Driven Activation of β2-Adrenergic Receptor Signaling by a Chimeric Rhodopsin Containing the β2-Adrenergic Receptor Cytoplasmic Loops," Biochemistry, 2005, vol. 44, No. 7, pp. 2284-2292.

Kingston et al. "Transfection of DNA into Eukaryotic Cells," Supplement 63, Current Protocols in Molecular Biology, 1996, 9.1.1-9.1.11, 11 pages.

Kingston et al. "Transfection and Expression of Cloned DNA," Supplement 31, Current Protocols in Immunology, 1999, 10.13.1-10.13.9.

Kita, H. et al. "Effects of dopamine agonists and antagonists on optical responses evoked in rat frontal cortex slices after stimulation of the subcortical white matter," Exp. Brain Research, 1999, vol. 125, pp. 383-388.

Kitayama, et al. "Regulation of neuronal differentiation by N-methyl-D-aspartate receptors expressed in neural progenitor cells isolated from adult mouse hippocampus," Journal of Neurosci Research, 2004, vol. 76, No. 5: pp. 599-612.

Klausberger, et al. "Brain-state- and cell-type-specific firing of hippocampal interneurons in vivo", Nature, 2003, vol. 421: pp. 844-848.

Kocsis et al., "Regenerating Mammalian Nerve Fibres: Changes in Action Potential Wavefrom and Firing Characteristics Following Blockage of Potassium Conductance", 1982, Proc. R. Soc. Lond., vol. B 217: pp. 77-87.

Kuhlman et al. (2008) "High-Resolution Labeling and Functional Manipulation of Specific Neuron Types in Mouse Brain by Cre-Activated Viral Gene Expression" PLoS One, 2005, vol. 3, No. 4, pp. 1-11.

Kunkler, P. et at. "Optical Current Source Density Analysis in Hippocampal Organotypic Culture Shows that Spreading Depression Occurs with Uniquely Reversing Current," The Journal of Neuroscience, 2005, vol. 25, No. 15, pp. 3952-3961.

Landy, A. "Mechanistic and structural complexity in the site-specific recombination pathways of Int and FLP", Current Opinion in Genetics and Development, 1993, vol. 3, pp. 699-707.

Lee et al. "Sterotactic Injection of Adenoviral Vectors that Target Gene Expression to Specific Pituitary Cell Types: Implications for Gene Therapy", Neurosurgery, 2000, vol. 46, No. 6: pp. 1461-1469.

Lee et al., "Potassium Channel Gone Therapy Can Prevent Neuron Deatch Resulting from Necrotic and Apoptotic Insults", Journal of Neurochemistry, 2003, vol. 85: pp. 1079-1088.

Levitan et al. "Surface Expression of Kv1 Voltage-Gated K+ Channels Is Governed by a C-terminal Motif," Trends Cardiovasc. Med., 2000, vol. 10, No. 7, pp. 317-320.

Li et al. "Fast noninvasive activation and inhibition of neural and network activity by vertebrate rhodopsin and green algae channelrhodopsin." PNAS, 2005, vol. 102, No. 49, p. 17816-17821.

Lim et al., "A Novel Targeting Signal for Proximal Clustering of the Kv2.1K+ Channel in Hippocampal Neurons", Neuron, 2000, vol. 25: pp. 385-397.

Lima, et al. "Remote Control of Behavior through Genetically Targeted Photostimulation of Neurons", Cell, 2005, vol. 121: pp. 141-152.

Liman, et al. "Subunit Stoichiometry of a Mammalian K+ Channel Determined by Construction of Multimeric cDNAs," Neuron, 1992,vol. 9, pp. 861-871.

Louis et al. "Cloning and sequencing of the cellular-viral junctions from the human adenovirus type 5 transformed 293 cell line," Virology, 1997, vol. 233, pp. 423-429.

Luecke, et al. "Structural Changes in Bacteriorhodopsin During Ion Transport at 2 Angstrom Resolution," Science, 1999, vol. 286, pp. 255-260.

Lyznik, et al. "FLP-mediated recombination of FRT sites in the maize genome," Nucleic Acids Research, 1996, vol. 24, No. 19: pp. 3784-3789.

Ma et al. "Role of ER Export Signals in Controlling Surface Potassium Channel Numbers," Science, 2001, vol. 291, pp. 316-319.

Mann et at. "Perisomatic Feedback Inhibition Underlies Cholinergically Induced Fast Network Oscillations in the Rat Hippocampus in Vitro," Neuron, 2005, vol. 45, 2005, pp. 105-117.

Mattson, "Apoptosis in Neurodegenerative Disorders", Nature Reviews, 2000, vol. 1: pp. 120-129.

Mayberg et al. "Deep Brain Stimulation for Treatment-Resistant Depression," Focus, 2008, vol. VI, No. 1, pp. 143-154.

McKnight "Functional relationships between transcriptional control signals of the thymidine kinase gene of herpes simplex virus", Cell, 1982, vol. 31 pp. 355-365.

Melyan, Z., et al. "Addition of human melanopsin renders mammalian cells Photoresponsive", Nature, 2005, vol. 433: pp. 741-745.

Mermelstein, et al. "Critical Dependence of cAMP Response Element-Binding Protein Phosphorylation on L-Type Calcium Channels Supports a Selective Response to EPSPs in Preference to Action Potentials", The Journal of Neuroscience, 2000, vol. 20, No. 1, pp. 266-273.

Meyer, et al. "High density interconnects and flexible hybrid assemblies for active biomedical implants," IEEE Transactions on Advanced Packaging, 2001, vol. 24, No. 3, pp. 366-372.

Monje et al., "Irradiation Induces Neural Precursor-Cell Dysfunction", Natural Medicine, 2002, vol. 8, No. 9, pp. 955-962.

Mortensen et al. "Selection of Transfected Mammalian Cells," Supplement 86, Current Protocols in Molecular Biology, 1997, 9.5.1-09.5.19.

Nacher, et al. "NMDA receptor antagonist treatment increases the production of newneurons in the aged rat hippocampus", Neurobiology of Aging, 2003,vol. 24, No. 2: pp. 273-284.

Nagel et al."Functional Expression of Bacteriorhodopsin in Oocytes Allows Direct Measurement of Voltage Dependence of Light Induced H+ Pumping," FEBS Letters, 1995, vol. 377, pp. 263-266.

Nagel, et al. "Channelrhodopsin-I: a light-gated proton channel in green algae", Science, 2002, vol. 296: pp. 2395-2398.

Nagel, et al. "Channelrhodopsin-2, a directly light-gated cation-selective membrane channel", PNAS, 2003, vol. 100, No. 24: pp. 13940-13945.

Nakagami, et al. "Optical Recording of Trisynaptic Pathway in Rat Hippocampal Slices with a Voltage-Sensitive Dye" Neuroscience, 1997, vol. 81, No. 1, pp. 1-8.

Naqvi, et al. "Damage to the insula disrupts addiction to cigarette smoking," Science; 2007, vol. 315 pp. 531-534.

Nirenberg, et al. "The Light Response of Retinal Ganglion Cells is Truncated by a Displaced Amacrine Circuit", Neuron, 1997, vol. 18: pp. 637-650.

Nunes-Duby, et al. "Similarities and differences among 105 members of the Int family of site-specific recombinases", Nucleic Acids Research, 1998, vol. 26, No. 2: pp. 391-406.

O'Gorman et al. "Recombinase-mediated gene activation and site-specific integration in mammalian cells", Science, 1991, 251(4999): pp. 1351-1355.

Olivares (2001) "Phage R4 integrase mediates site-specific integration in human cells", Gene, 2001, vol. 278, pp. 167-176.

Ory, et al. "A stable human-derived packaging cell line for production of high titer retrovirus/vesicular stomatitis virus G pseudotypes," PNAS, 1996, vol. 93: pp. 11400-11406.

Palmer et al., "The Adult Rat Hippocampus Contains Primordial Neural Stem Cells", Molecular and Cellular Neuroscience, 1997, vol. 8, pp. 389-404.

Palmer et al., "Fibroblast Growth Factor-2 Activates a Latent Neurogenic Program in Neural Stem Cells from Diverse Regions of the Adult CNS", The Journal of Neuroscience, 1999, vol. 19, pp. 8487-8497.

Pan et al. "Functional Expression of a Directly Light-Gated Membrane Channel in Mammalian Retinal Neurons: A Potential Strategy

(56) References Cited

OTHER PUBLICATIONS for Restoring Light Sensitivity to the Retina After Photoreceptor Degeneration," Investigative Opthalmology & Visual Science, 2005, 46 E-Abstract 4631. Abstract only.
Panda, et al. " Illumination of the Melanopsin Signaling Pathway", Science, 2005, vol. 307: pp. 660-604.
Paulhe et al. "Specific Endoplasmic Reticulum Export Signal Drives Transport of Stem Cell Factor (Kitl) to the Cell Surface," The Journal of Biological Chemistry, 2004, vol. 279, No. 53, p. 55545-55555.
Pear "Transient Transfection Methods for Preparation of High-Titer Retroviral Supernatants" Supplement 68, Current Protocols in Molecular Biology, 1996, 9.1 1 .I -9.1 1 .I 8.
Petersen et al. "Spatiotemporal Dynamics of Sensory Responses in Layer 2/3 of Rat Barrel Cortex Measured In Vivo by Voltage-Sensitive Dye Imaging Combined with Whole-Cell Voltage Recordings and Neuron Reconstructions," The Journal of Neuroscience, 2003, vol. 23, No. 3, pp. 1298-1309.
Petrecca, et al. "Localization and Enhanced Current Density of the Kv4.2 Potassium Channel by Interaction with the Actin-Binding Protein Filamin," The Journal of Neuroscience, 2000, vol. 20, No. 23, pp. 8736-8744.
Pettit, et al. "Local Excitatory Circuits in the Intermediate Gray Layer of the Superior Colliculus", J Neurophysiol., 1999, vol. 81, No. 3: pp. 1424-1427.
Potter, "Transfection by Electroporation." Supplement 62, Current Protocols in Molecular Biology, 1996, 9.3.1-9.3.6.
Pouille, et al. "Routing of spike series by dynamic circuits in the hippocampus", Nature, 2004, vol. 429: pp. 717-723.
Qiu et al. "Induction of photosensitivity by heterologous expression of melanopsin", Nature, 2005, vol. 433: pp. 745-749.
Rathnasingham et al., "Characterization of implantable microfabricated fluid delivery devices," IEEE Transactions on Biomedical Engineering, 2004, vol. 51, No. 1: pp. 138-145.
Rivera et al., "BDNF-Induced TrkB Activation Down-Regulates the K+-Cl-cotransporter KCC2 and Impairs Neuronal Cl-Extrusion", The Journal of Cell Biology, 2002, vol. 159: pp. 747-752.
Rosenkranz, et al. "The prefrontal cortex regulates lateral amygdala neuronal plasticity and responses to previously conditioned stimuli", J. Neurosci., 2003, vol. 23, No. 35: pp. 11054-11064.
Rousche, et al., "Flexible polyimide-based intracortical electrode arrays with bioactive capability," IEEE Transactions on Biomedical Engineering, 2001, vol. 48, No. 3, pp. 361-371.
Rubinson et at. "A lentivirus-based system to functionally silence genes in primary mammalian cells, stem cells and transgenic mice by RNA interference," Nature Genetics, 2003, vol. 33, p. 401-406.
Rudiger et at. "Specific arginine and threonine residues control anion binding and transport in the light-driven chloride pump halorhodopsin," The EMBO Journal, 1997, vol. 16, No. 13, pp. 3813-3821.
Salzman, et al. "Cortical microstimulation influences perceptual judgements of motion direction", Nature, 1990, vol. 346, pp. 174-177.
Sato et al. "Role of Anion-binding Sites in cytoplasmic and extracellular channels of *Natronomonas pharaonis* halorhodopsin," Biochemistry, 2005. vol. 44, pp. 4775-4784.
Sauer "Site-specific recombination: developments and applications," Current Opinion in Biotechnology, 1994, vol. 5, No. 5: pp. 521-527.
Schiff, et al. "Behavioral improvements with thalamic stimulation after severe traumatic brain injury," Nature, 2007, vol. 448, pp. 600-604.
Schlaepfer et al. "Deep Brain stimulation to Reward Circuitry Alleviates Anhedonia in Refractory Major Depression," Neuropsychopharmacology, 2008,vol. 33, pp. 368-377.
Sclimenti, et al. "Directed evolution of a recombinase for improved genomic integration at a native human sequence," Nucleic Acids Research, 2001, vol. 29, No. 24: pp. 5044-5051.
Shepherd, et al. "Circuit Analysis of Experience-Dependent Plasticity in the Developing Rat Barrel Cortex", Neuron, 2003, vol. 38: pp. 277-289.
Silver, et al. "Amino terminus of the yeast *GAL4* gene product is sufficient for nuclear localization" PNAS, 1984, vol. 81, No. 19: pp. 5951-5955.
Singer et al. "Elevated lntrasynaptic Dopamine Release in Tourette's Syndrome Measured by PET," American Journal of Psychiatry, 2002, vol. 159: pp. 1329-1336.
Slimko et al., "Selective Electrical Silencing of Mammalian Neurons In Vitro by the use of Invertebrate Ligand-Gated Chloride Channels", The Journal of Neuroscience, 2002, vol. 22, No. 17: pp. 7373-7379.
Smith et al. "Diversity in the serine recombinases", Molecular Microbiology, 2002, vol. 44, No. 2: pp. 299-307.
Song et al. "Differential Effect of TEA on Long-Term Synaptic Modification in Hippocampal CA1 and Dentate Gyrus in vitro." Neurobiology of Learning and Memory, 2001, vol. 76, No. 3, pp. 375-387.
Song, "Genes responsible for native depolarization-activated K+ currents in neurons," Neuroscience Research, 2002, vol. 42, pp. 7-14.
Stark, et al. "Catalysis by site-specific recombinases," Trends Genet., 1992, vol. 8, No. 12: pp. 432-439.
Stockklausner et al. "A sequence motif responsible for ER export and surface expression of Kir2.0 inward rectifier K+ channels," FEBS Letters, 2001, vol. 493, pp. 129-133.
Stoll, et al. "Phage TP901-I site-specific integrase functions in human cells," Journal of Bacteriology, 2002, vol. 184, No. 13: pp. 3657-3663.
Takahashi, et al."Diversion of the Sign of Phototaxis in a *Chlamydomonas reinhardtii* Mutant Incorporated with Retinal and Its Analogs," FEBS Letters, 1992, vol. 314, No. 3, pp. 275-279.
Tatarkiewicz, et al. "Reversal of Hyperglycemia in Mice After Subcutaneous Transplantation of Macroencapsulated Islets", Transplantation, 1999, vol. 67, No. 5: pp. 665-671.
Tottene et al., "Familial Hemiplegic Migraine Mutations Increase $Ca^{2+}$ Influx Through Single Human $Ca_v2.1$ Current Density in Neurons", PNAS USA, 2002, vol. 99, No. 20: pp. 13284-13289.
Tsau et al. "Distributed Aspects of the Response to Siphon Touch in *Aplysia*: Spread of Stimulus Information and Cross-Correlation Analysis," The Journal of Neuroscience, 1994, vol. 14, No. 7, pp. 4167-4184.
[No Authors Listed] "Two bright new faces in gene therapy," Nature Biotechnology, 1996, vol. 14: p. 556.
Tye et. al., "Amygdala circuitry mediating reversible and bidirectional control of anxiety", Nature, 2011, vol. 471(7338): pp. 358-362.
Tye et. al., Supplementary Materials: "An optically-resolved microcircuit for bidirectional anxiety control", Nature, 2011, vol. 471(7338): pp. 358-362.
Ulmanen, et al. "Transcription and translation of foreign genes in *Bacillus subtilis* by the aid of a secretion vector," Journal of Bacteriology, 1985, vol. 162, No. 1: pp. 176-182.
Van Der Linden, "Functional brain imaging and pharmacotherapy in social phobia: single photon emission computed tomography before and after Treatment with the selective serotonin reuptake inhibitor citalopram," Prog Neuro-psychopharmacol Biol Psychiatry, 2000, vol. 24, No. 3: pp. 419-438.
Vanin, et al. "Development of high-titer retroviral producer cell lines by using Cre-mediated recombination," Journal of Virology, 1997, vol. 71, No. 10: pp. 7820-7826.
Vetter, et al. "Development of a Microscale Implantable Neural Interface (MINI) Probe System," Proceedings of the 2005 IEEE, Engineering in Medicine and Biology 27th Annual Conference, Shanghai, China, Sep. 1-4, 2005.
Wagner, "Noninvasive Human Brain Stimulation", Annual Rev. Biomed. Eng. 2007. 9:19.1-19.39.
Ward, et al. "Construction and characterisation of a series of multi-copy promoter-probe plasmid vectors for *Streptomyces* using the aminoglycoside phosphotransferase gene from Tn5 as indicator", 1986, Mol. Gen. Genet., vol. 203: pp. 468-478.

(56) References Cited

OTHER PUBLICATIONS

Watson, et al. "Targeted transduction patterns in the mouse brain by lentivirus vectors pseudotyped with VSV, Ebola, Mokola, LCMV, or MuLV envelope proteins," Molecular Therapy, 2002, vol. 5, No. 5, pp. 528-537.
Wang et. al., "High-speed mapping of synaptic connectivity using photostimulation in Channelrhodopsin-2 transgenic mice", PNAS, 2007, vol. 104, No. 19, pp. 8143-8148.
Weick et al. "Interactions with PDZ Proteins Are Required for L-Type Calcium Channels to Activate cAMP Response Element-Binding Protein-Dependent Gene Expression," The Journal of Neuroscience, 2003, vol. 23, No. 8, pp. 3446-3456.
Wells et al. "Application of Infrared light for in vivo neural stimulation," Journal of Biomedical Optics, 2005, vol. 10(6), pp. 064003-1-064003-12.
Witten et. al., Supporting Online Material for: "Cholinergic Interneurons Control Local Circuit Activity and Cocaine Conditioning", Science, 2010, vol. 330: 17 pages.
Witten et. al., "Cholinergic Interneurons Control Local Circuit Activity and Cocaine Conditioning", Science, 2010, vol. 330, No. 6011: pp. 1677-1681.
Yamazoe, et al. "Efficient generation of dopaminergic neurons from mouse embryonic stem cells enclosed in hollow fibers", Biomaterials, 2006, vol. 27, pp. 4871-4880.
Yan et al., "Cloning and Characterization of a Human β,β-Carotene-15, 15'-Dioxygenase that is Highly Expressed in the Retinal Pigment Epithelium", Genomics, 2001, vol. 72: pp. 193-202.
Yizhar et. al., "Neocortical excitation/inhibition balance in information processing and social dysfunction", Nature, 2011, vol. 477, pp. 171-178; and Supplemental Materials; 41 pages.
Yoon, et al., "A micromachined silicon depth probe for multichannel neural recording," IEEE Transactions Biomedical Engineering, 2000, vol. 47, No. 8, pp. 1082-1087.
Yoshimura, et al. "Excitatory cortical neurons form fine-scale functional networks", Nature, 2005, vol. 433: pp. 868-873.
Zacharias et al. "Recent advances in technology for measuring and manipulating cell signals," Current Opinion in Neurobiology, 2000, vol. 10: pp. 416-421.
Zemelman, et al. "Selective Photostimulation of Genetically ChARGed Neurons", Neuron, 2002, vol. 33: pp. 15-22.
Zemelman, et al. "Photochemical gating of heterologous ion channels: Remote control over genetically designated populations of neurons", PNAS, 2003, vol. 100, No. 3: pp. 1352-1357.
Zhang, et al. "Channelrhodopsin-2 and optical control of excitable cells," Nature Methods,2006, vol. 3, No. 10, pp. 785-792.
Zhang, et al. "Red-Shifted Optogenetic Excitation: a Tool for Fast Neural Control Derived from *Volvox carteri*", Nature Neurosciences, 2008,vol. 11, No. 6, pp. 631-633.
Zhang "Multimodal fast optical interrogation of neural circuitry," Nature, 2007, vol. 446, pp. 633-641.
Zrenner, E., "Will Retinal Implants Restore Vision?" Science, 2002, vol. 295, No. 5557, pp. 1022-1025.
Zufferey, et al. "Self-Inactivating Lentivirus Vector for Safe and Efficient In Vivo Gene Delivery", Journal of Virology, 1998, vol. 72, No. 12, pp. 9873-9880.
Tam, B. et al., "Identification of an Outer Segment Targeting Signal in the CoOH Terminus of Rhodopsin Using Transgenic Xenopus laevis", The Journal of Cell Biology, 2000, vol. 151, No. 7, pp. 1369-1380.
Pear "Transient Transfection Methods for Preparation of High-Titer Retroviral Supernatants" Supplement 68, Current Protocols in Molecular Biology, 1996, 9.1 1 .I-9.1 1 .I 8.
Cazillis et al., "VIP and PACAP induce selective neuronal differentiation of mouse embryonic stem cells", Eur J Neurosci, 2004, 19(4):798-808.
Morelli et al. "Neuronal and glial cell type-specific promoters within adenovirus recombinants restrict the expression of the apoptosis-inducing molecule Fas ligand to predetermined brain cell types, and abolish peripheral liver toxicity", Journal of General Virology, 1999, 80:571-583.

Berke, et al. "Addiction, Dopamine, and the Molecular Mechanisms of Memory", Molecular Plasticity, 2000, vol. 25: pp. 515-532.
Goshen et al. "Dynamics of Retrieval Strategies for Remote Memories", Cell, 2011, vol. 147: pp. 678-589.
Jimenez S.A & Maren S. et al/ "Nuclear disconnection within the amygdala reveals a direct pathway to fear", Learning Memory, 2009, vol. 16: pp. 766-768.
Ehrlich I. et al. "Amygdala inhibitory circuits and the control of fear memory", Neuron, 2009. Friedrich Meischer Institute, vol. 62: pp. 757-771.
Berndt et al. "Bi-stable neural state switches", Nature Neuroscience, 2009, vol. 12, No. 2: pp. 229-234.
Simmons et al. "Localization and function of NK3 subtype Tachykinin receptors of layer pyramidal neurons of the guinea-pig medial prefrontal cortex", Neuroscience, 2008, vol. 156, No. 4: pp. 987-994.
Gradinaru, et al., Molecular and Cellular Approaches for Diversifying and Extending Optogenetics, Cell, 2010, vol. No. 1, pp. 154-165.
RecName: Full=Halorhodopsin; Short=HR; Alt Name: Full=NpHR; XP002704922, retrieved from EBI accession No. UNIPROT: P15647. Database accession No. P15647. Apr. 1, 1990.
"N. pharaonis halorhodopsin (hop) gene, complete cds.", XP002704883, retrieved from EBI accession No. EMBL: J05199. Database accession No. J05199. Nov. 22, 1990.
"Subname: Fluu= Bacteriorhodopsin"; XP002704863, retrieved from EBI accession No. UNIPROT: B0R5N9. Database accession No. B0R5N9. Apr. 8, 2008.
Zhang, et al., "The Microbial Opsin Family of Optogenetic Tools", Cell, 2011, vol. 147, No. 7, pp. 1146-1457.
Adamantidis, et al., "Optogenetic Interrogation of Dopaminergic Modulation of the Multiple Phases of Reward-Seeking Behavior", J. Neurosci, 2011, vol. 31, No. 30, pp. 10829-10835.
Han, et al., "Multiple-Color Optical Activation, Silencing, and Desynchronization of Neural Activity with Single-Spike Temporal Resolution", PLoS One, 2007, vol. 2, No. 3, pp. 1-12.
Kinoshita, et al., "Optogenetically Induced Supression of Neural Activity in the Macaque Motor Cortex", Poster Sessions Somatomotor System, Others,2010, pp. 141-154.
Rein, et al., "The Optogenetic (r)evolution", Mol. Genet. Genomics, 2012, vol. 287, No. 2, pp. 95-109.
Remy, et al., "Depression in Parkinson's Disease: Loss of Dopamine and Noradrenaline Innervation in the Limbic System", Brain, 2005, vol. 128 (Pt 6), pp. 1314-1322.
Tsai, et al., "Phasic Firing in Dopaminergic Neurons in Sufficient for Behavioral Conditioning", Science, 2009, vol. 324, pp. 1080-1084.
Zhao, et al., "Improved Expression of Halorhodopsin for Light-Induced Silencing of Neuronal Activity", Brain Cell Biology, 2008, vol. 36 (1-4), pp. 141-154.
Lanyi et al. "The primary structure of a Halorhodopsin from *Natronobacterium Pharaonis*" Journal of Biological Chemistry 1990, vol. 265, No. 3, p. 1253-1260.
Hofherr et al. "Selective Golgi export of Kir2.1 controls the stoichiometry of functional Kir2.x channel heteromers" Journal of Cell Science, 2005, vol. 118, p. 1935-1943.
Loetterle, et al., "Cerebellar Stimulation: Pacing the Brain", American Journal of Nursing, 1975, vol. 75, No. 6, pp. 958-960.
Xiong et al., "Interregional connectivity to primary motor cortex revealed using MRI resting state images", Hum Brain Mapp, 1999, 8(2-3):151-156.
Li et al., "Surface Expression of Kv1 Channels is Governed by a C-Terminal Motif", J. Bioi. Chem. (2000), 275(16):11597-11602.
Lonnerberg et al. "Regulatory Region in Choline Acetyltransferase Gene Directs Developmental and Tissue-Specific Expression in Transgenic mice", Proc. Natl. Acad. Sci. USA (1995), 92(9):4046-4050.
Varo et al.,"Light-Driven Chloride Ion Transport by Halorhodopsin from Natronobacterium pharaonis. 2. Chloride Release and Uptake, Protein Conformation Change, and Thermodynamics", Biochemistry (1995), 34(44):14500-14507.
Deisseroth, et al., "Controlling the Brain with Light", Scientific American, 2010, vol. 303, pp. 48-55.

(56) References Cited

OTHER PUBLICATIONS

Douglass, et al., "Escape Behavior Elicited by Single, Channelrhodopsin-2-evoked Spikes in Zebrafish Somatosensory Neurons", Curr Biol., 2008, vol. 18, No. 15, pp. 1133-1137.
Sineshchekov, et al., "Two Rhodopsins Mediate Phototaxis to Low and High Intensity Light in Chlamydomas Reinhardtil", PNAS, 2002, vol. 99, No. 13, pp. 8689-8694.
Tønnese, et al., "Optogenetic Control of Epileptiform Activity", PNAS, 2009, vol. 106, No. 29, pp. 12162-12167.
Babin et al., "Zebrafish Models of Human Motor Neuron Diseases: Advantages and Limitations", Progress in Neurobiology (2014), 118:36-58.
Santana et al., "Can Zebrafish Be Used as Animal Model to Study Alzheimer's Disease?" Am. J. Neurodegener. Dis. (2012), 1(1):32-48.
Sheikh et al., "Neurodegenerative Diseases: Multifactorial Conformational Diseases and Their Therapeutic Interventions", Journal of Neurodegenerative Diseases (2013), Article ID 563481:1-8.
Suzuki et al., "Stable Transgene Expression from HSV Amplicon Vectors in the Brain: Potential Involvement of Immunoregulatory Signals", Molecular Therapy (2008), 16(10):1727-1736.
Thomas et al., "Progress and Problems with the Use of Viral Vectors for Gene", Nat. Rev. Genet. (2003), 4(5):346-358.
Delaney et al., "Evidence for a long-lived 13-cis-containing intermediate in the photocycle of the leu 93 → ala bacteriorhodopsin mutant", J. Physical Chemistry B, 1997, vol. 101, No. 29, pp. 5619-5621.
Fenno et al., "The development and application of optogenetics", Annual Review of Neuroscience, 2011, vol. 34, No. 1, pp. 389-412.
Gunaydin et al., "Ultrafast optogenetic control", Nature Neuroscience, 2010, vol. 13, No. 3, pp. 387-392.
Hira et al., "Transcranial optogenetic stimulation for functional mapping of the motor cortex", J Neurosci Methods, 2009, vol. 179, pp. 258-263.
Lalumiere, R., "A new technique for controlling the brain: optogenetics and its potential for use in research and the clinic", Brain Stimulation, 2011, vol. 4, pp. 1-6.
Lin, "A user's guide to channelrhodopsin variants: features, limitations and future developments", Exp Physiol, 2010, vol. 96, No. 1, pp. 19-25.
Mancuso et al., "Optogenetic probing of functional brain circuitry", Experimental Physiology, 2010, vol. 96.1, pp. 26-33.
Peralvarez-Marin et al., "Inter-helical hydrogen bonds are essential elements for intra-protein signal transduction: The role of Asp115 in bacteriorhodopsin transport function", J. Mol. Biol., 2007, vol. 368, pp. 666-676.
Pinkham et al., "Neural bases for impaired social cognition in schizophrenia and autism spectrum disorders", Schizophrenia Research, 2008, vol. 99, pp. 164-175.
Sohal et al., "Parvalbumin neurons and gamma rhythms enhance cortical circuit performance", Nature, 2009, vol. 459, No. 7247, pp. 698-702.
Yizhar et al., "Optogenetics in neural systems", Neuron Primer, 2011, vol. 71, No. 1, pp. 9-34.
Gradinaru et al., "Targeting and readout strategies for fast optical neural control in vitro and in vivo", J Neuroscience, 2007, 27(52):14231-14238.
Berndt et al., "Structure-Guided Transformation of Channelrhodopsin into a Light-Activated Chloride Channel", Science (Apr. 2014), 344(6182):420-424.
Chow et al., "Optogenetics and Translational Medicine", Science Translational Medicine (Mar. 2013), 5(177):177ps5.
Eijkelkamp, et al. "Neurological perspectives on voltage-gated sodium channels", Brain (Sep. 2012), 135(Pt 9):2585-2612.
Garrido et al., "A targeting motif involved in sodium channel clustering at the axonal initial segment", Science (Jun. 2003), 300(5628):2091-4.

Han; et al., "Two-color, bi-directional optical voltage control of genetically-targeted neurons", CoSyne (2007), Abstract Presentation, Poster III-67, p. 269, Presented Feb. 24, 2007.
Hustler; et al., "Acetylcholinesterase staining in human auditory and language cortices: regional variation of structural features", Cereb Cortex (Mar.-Apr. 1996), 6(2):260-70.
Iyer et al., "Virally mediated optogenetic excitation and inhibition of pain in freely moving nontransgenic mice", Nat Biotechnol., (Mar. 2014), 32(3):274-8.
Ji et al., "Light-evoked Somatosensory Perception of Transgenic Rats that Express Channelrhodopsin-2 in Dorsal Root Ganglion Cells", PLoS One (2012), 7(3):e32699.
Jennings et al., "Distinct extended amygdala circuits for divergent motivational states," Nature (Apr. 2013), 496 (7444):224-8.
Kim et al., "PDZ domain proteins of synapses", Nature Reviews Neuroscience, (Oct. 2004), 5(10):771-81.
Kim et al., "Diverging neural pathways assemble a behavioural state from separable features in anxiety" Nature (Apr. 2013), 496(7444):219-23.
Kokel et al., "Photochemical activation of TRPA1 channels in neurons and animals", Nat Chem Biol (Apr. 2013), 9(4):257-63.
Lammel et al., "Input-specific control of reward and aversion in the ventral tegmental area", Nature (Nov. 2012), 491 (7423): 212-7.
Liske et al., "Optical inhibition of motor nerve and muscle activity in vivo", Muscle Nerve (Jun. 2013), 47(6):916-21.
Llewellyn et al., "Orderly recruitment of motor units under optical control in vivo", Nature Medicine, (Oct. 2010), 16 (10):1161-5.
Mattis et al., "Principles for applying optogenetic tools derived from direct comparative analysis of microbial opsins", Nat Methods (Dec. 2011), 9(2):159-72.
Mourot et al., "Rapid Optical Control of Nociception with an Ion Channel Photoswitch", Nat Methods (Feb. 2012), 9 (4):396-402.
Nieh et al., "Optogenetic dissection of neural circuits underlying emotional valence and motivated behaviors", Brain Research, (May 2012), 1511:73-92.
Slamovits et al., "A bacterial proteorhodopsin proton pump in marie eukaryotes", Nature Communications (Feb. 2011), 2:183.
Towne et al., "Efficient transduction of non-human primate motor neurons after intramuscular delivery of recombinant AAV serotype 6", Gene Ther. (Jan. 2010), 17(1):141-6.
Towne et al., "Optogenetic control of targeted peripheral axons in freely moving animals", PLoS One (Aug. 2013), 8 (8):e72691.
Towne et al., "Recombinant adeno-associated virus serotype 6 (rAAV2/6)-mediated gene transfer to nociceptive neurons through different routes of delivery", Mol Pain (Sep. 2009), 5:52.
Wang et al., "Mrgprd-Expressing Polymodal Nociceptive Neurons Innervate Most Known Classes of Substantia Gelatinosa Neurons", J Neurosci (Oct. 2009), 29(42):13202-13209.
Williams et al., "From optogenetic technologies to neuromodulation therapies", Sci Transl Med. (Mar. 2013), 5 (177):177ps6.
Ageta-Ishihara et al., "Chronic overload of SEPT4, a parkin substrate that aggregates in Parkinson's disease, cause behavioral alterations but not neurodegeneration in mice", Molecular Brain, 2013, vol. 6, 14 pages.
Axoclamp-28 Microelectrode claim theory and operation. Accessed from https://physics.ucsd.edu/neurophysics/Manuals/Axon%20Instruments/Axoclamp-2B_Manual.pdf on Dec. 12, 2014.
Cowan et al., "Targeting gene expression to endothelium in transgenic animals: a comparison of the human ICAM-2, PECAM-1, and endoglin promoters", Xenotransplantation, 2003, vol. 10, pp. 223-231.
Definition of Psychosis (2015).
Ebert et al., "A Moloney MLV-rat somatotropin fusion gene produces biologically active somatotropin in a transgenic pig", Mol. Endocrinology, 1988, vol. 2, pp. 277-283.
Hammer et al., "Spontaneous inflammatory disease in transgenic rats expressing HLA-B27 and Human $\beta_2$m: an animal model of HLA-B27-associated human disorders", Cell, 1990, vol. 63, pp. 1099-1112.
Karra, et al. "Transfection Techniques for Neuronal Cells", The Journal of Neuroscience, 2010, vol. 30, No. 18, pp. 6171-6177.

(56) References Cited

OTHER PUBLICATIONS

Kelder et al., "Glycoconjugates in human and transgenic animal milk", Advances in Exp. Med. and Biol., 2001, vol. 501, pp. 269-278.
Mullins et al., "Fulminant hypertension in transgenic rats harbouring the mouse Ren-2 gene", Nature, 1990, vol. 344, pp. 541-544.
Mullins et al., "Expression of the DBA/2J Ren-2 gene in the adrenal gland of transgenic mice", EMBO, 1989, vol. 8, pp. 4065-4072.
Shibasaki et al., "Effects of body temperature on neural activity in the hippocampus: Regulation of resting membrane potentials by transient receptor potential vanilloid 4," The Journal of Neuroscience, 2007, 27(7):1566-1575.
Takahashi, et al., "Induction of Pluripotent Stem Cells from Mouse Embryonic and Adult Fibroblast Cultures by Defined Factors", 2006, Cell, vol. 126, pp. 663-676.
Taurog et al., "HLA-B27 in inbred and non-inbred transgenic mice", J. Immunol., 1988, vol. 141, pp. 4020-4023.
Wall, "Transgenic livestock: Progress and prospects for the future", Theriogenology, 1996, vol. 45, pp. 57-68.
Wang, et al., "High-speed mapping of synaptic connectivity using photostimulation in Channelrhodopsin-2 transgenic mice", Proceedings of the National Academy of Sciences, 2007, vol. 104, No. 19, pp. 8143-8148.
Written opinion of PCT Application No. PCT/US2011/059383 (dated May 9, 2012).
Han, et al., "Millisecond-Timescale Optical Control of Neural Dynamics in the Nonhuman Primate Brain"; Neuron; vol. 62, pp. 191-198 (Apr. 30, 2009).
Han, et a.; "Virogenetic and optogenetic mechanisms to define potential therapeutic targets in psychiatric disorders"; Neuropharmacology; vol. 62, pp. 89-100 (2012).
Zhang, et al.; "Optogenetic interrogation of neural circuits: Technology for probing mammalian brain structures"; Nature Protocols; vol. 5, No. 3, pp. 439-456 (Mar. 1, 2010).
Davis; "The many faces of epidermal growth factor repeats," The New Biologist; vol. 2, No. 5, pp. 410-419 (1990).
De Palma, et al.; "In Vivo Targeting of Tumor Endothelial Cells by Systemic Delivery of Lentiviral Vectors"; Human Gene Therapy; vol. 14, pp. 1193-1206 (Aug. 10, 2003).
EBI accession No. UNIPROT: A7U0Y6; "SubName: Full=Bacteriorhodopsin"; (Aug. 10, 2010).
Ghebremariam, et al.; "A Novel and Potent Inhibitor of Dimethylarginine Dimethylaminohydrolase: A Modulator of Cardiovascular Nitric Oxide"; Journal of Pharmacology and Experimental Therpeutics; vol. 348, No. 1, pp. 69-76 (Dec. 14, 2013).
Ghebremariam, et al.; "Development of a Dimethylarginine Dimethylaminohydrolase (DDAH) Assay for High-Throughput Chemical Screening"; Journal of Biomolecular Screening Society for Laboratory Automation and Screening; vol. 17, No. 5, pp. 651-664 (Mar. 29, 2012).
Ihara, et al.; "Evolution of the Archaeal Rhodopsins: Evolution Rate Changes by Gene Duplication and Functional Differentiation"; J. Mol. Biol.; vol. 285, pp. 163-174 (1999).
Kaiser; "Clinical research. Death prompts a review of gene therapy vector"; Science; 317(5838):580 (Aug. 3, 2007).
Kay; "State-of-the-art gene-based therapies: the road ahead"; Nature Reviews Genetics; vol. 12, pp. 316-328 (May 2011).
Raper, et al.; "Fatal systemic inflammatory response syndrome in a ornithine transcarbamylase deficient patient following adenoviral gene transfer." Mol. Genet. Metab.; vol. 80, No. 1-2, pp. 148-158 (Sep.-Oct. 2003).
Singer; "Light Switch for Bladder Control"; Technology Review; pp. 1-2 (Sep. 14, 2009).
Skolnick, et al.; "From genes to protein structure and function: novel applications of computational approaches in the genomic era"; Trends Biotechnol; vol. 18, No. 1, pp. 34-39 (Jan. 2000).
Soofiyani, et al.; "Gene Therapy, Early Promises, Subsequent Problems, and Recent Breakthroughs"; Advanced Pharmaceutical Bulletin; vol. 3, No. 2, pp. 249-255 (2013).

Brewin; "The Nature and Significance of Memory Disturbance in Posttraumatic Stress Disorder"; Ann. Rev. Clin. Psychol.; vol. 7, pp. 203-227 (2011).
Samuelson; "Post-traumatic stress disorder and declarative memory functioning: a review"; Dialogues in Clinical Neuroscience; vol. 13, No. 3, pp. 346-351 (2011).
Ali; "Gene and stem cell therapy for retinal disorders"; vision-research.en—The Gateway to European Vision Research; accessed from http://www.vision-research.eu/index.php?id=696, 10 pages. (accessed Jul. 24, 2015).
Asano, et al.; "Optically Controlled Contraction of Photosensitive Skeletal Muscle Cells"; Biotechnology & Bioengineering; vol. 109, No. 1, pp. 199-204 (Jan. 2012).
Bruegmann, et al.; "Optogenetic control of heart muscle in vitro and in vivo"; Nature Methods; vol. 7, No. 11, pp. 897-900(Nov. 2010).
Bruegmann, et al.; "Optogenetics in cardiovascular research: a new tool for light-induced depolarization of cardiomyocytes and vascular smooth muscle cells in vitro and in vivo"; European Heart Journal; vol. 32, No. Suppl . 1, p. 997 (Aug. 2011).
Genbank Accession No. AAG01180.1; Idnurm, et al.; pp. 1 (Mar. 21, 2001).
Genbank Accession No. ABT17417.1; Sharma, et al.; pp. 1 (Aug. 15, 2007).
Genbank Accession No. BAA09452.1; Mukohata et al.; pp. 1 (Feb. 10, 1999).
Kessler, et al.; "Gene delivery to skeletal muscle results in sustained expression and systemic delivery of a therapeutic protein"; Proc. Natl. Acad. Sci. USA; vol. 93, pp. 14082-14087 (Nov. 1996).
Mueller, et al.; "Clinical Gene Therapy Using Recombinant Adeno-Associated Virus Vectors"; Gene Therapy; vol. 15, pp. 858-863 (2008).
Wang, et al.; "Laser-evoked synaptic transmission in cultured hippocampal neurons expressing channelrhodopsin-2 delivered by adeno-associated virus"; Journal of Neuroscience Methods; vol. 183, pp. 165-175 (2009).
Clark, et al.; "A future for transgenic livestock"; Nature Reviews Genetics; vol. 4, No. 10, pp. 825-833 (Oct. 2003).
Do Carmo, et al.; "Modeling Alzheimer's disease in transgenic rats"; Molecular Neurodegeneration; vol. 8, No. 37, 11 pages (2013).
Heymann, et al.; "Expression of Bacteriorhodopsin in Sf9 and COS-1 Cells"; Journal of Bioenergetics and Biomembranes; vol. 29, No. 1, pp. 55-59 (1997).
Ramalho, et al.; "Mouse genetic corneal disease resulting from transgenic insertional mutagenesis"; Br. J. Ophthalmol.; vol. 88, No. 3, pp. 428-432 (Mar. 2004).
Ristevski; "Making Better Transgenic Models: Conditional, Temporal, and Spatial Approaches"; Molecular Biotechnology; vol. 29, No. 2, pp. 153-163 (Feb. 2005).
Sigmund; "Viewpoint: Are Studies in Genetically Altered Mice Out of Control?"; Arterioscler Thromb Vasc. Biol.; vol. 20, No, 6, pp. 1425-1429 (Jun. 2000).
Sineshchekov et al.; "Intramolecular Proton Transfer in Channelrhodopsins"; Biophysical Journal; vol. 104, No. 4, pp. 807-807 (Feb. 2013).
Airan, et al.; "Integration of light-controlled neuronal firing and fast circuit imaging"; Current Opinion in Neurobiology; vol. 17, pp. 587-592 (2007).
Cannon, et al.; "Endophenotypes in the Genetic Analyses of Mental Disorders"; Annu. Rev. Clin. Psychol.; vol. 2, pp. 267-290 (2006).
Chamanzar, et al.; "Deep Tissue Targeted Near-infrared Optogenetic Stimulation using Fully Implantable Upconverting Light Bulbs"; 2015 37th Annual International Conference of the IEEE Engineering in Medicine and Biology Society (EMBC), IEEE; doi: 10.1109/EMBC.2015.7318488, pp. 821-824 (Aug. 25, 2015).
Chinta, et al.; "Dopaminergic neurons"; The International Journal of Biochemistry & Cell Biology; vol. 37, pp. 942-946 (2005).
Deonarain; "Ligand-targeted receptor-mediated vectors for gene delivery"; Exp. Opin. Ther. Patents; vol. 8, No. 1, pp. 53-69 (1998).
Edelstein, et al.; "Gene therapy clinical trials worldwide 1989-2004—an overview"; The Journal of Gene Medicine; vol. 6, pp. 597-602 (2004).

(56) References Cited

OTHER PUBLICATIONS

Grady, et al.; "Age-Related Reductions in Human Recognition Memory Due to Impaired Encoding"; Science; vol. 269, No. 5221, pp. 218-221 (Jul. 14, 1995).
Hososhima, et al.; "Near-infrared (NIR) up-conversion optogenetics"; Optical Techniques in Neurosurgery, Neurophotonics, and Optogenetics II; vol. 9305, doi: 10.1117/12.2078875, 4 pages (2015).
Johnson-Saliba, et al.; "Gene Therapy: Optimising DNA Delivery to the Nucleus"; Current Drug Targets; vol. 2, pp. 371-399 (2001).
Palu, et al.; "In pursuit of new developments for gene therapy of human diseases"; Journal of Biotechnology; vol. 68, pp. 1-13 (1999).
Petersen, et al.; "Functionally Independent Columns of Rat Somatosensory Barrel Cortex Revealed with Voltage-Sensitive Dye Imaging"; J. of Neuroscience; vol. 21, No. 21, pp. 8435-8446 (Nov. 1, 2011).
Pfeifer, et al.; "Gene Therapy: Promises and Problems"; Annu. Rev. Genomics Hum. Genet.; vol. 2, pps. 177-211 (2001).
Powell, et al.; "Schizophrenia-Relevant Behavioral Testing in Rodent Models: A Uniquely Human Disorder?"; Biol. Psychiatry; vol. 59, pp. 1198-1207 (2006).
Shoji, et al.; "Current Status of Delivery Systems to Improve Target Efficacy of Oligonucleotides"; Current Pharmaceutical Design; vol. 10, pp. 785-796 (2004).
Verma, et al.; "Gene therapy—promises, problems and prospects"; Nature; vol. 389, pp. 239-242 (Sep. 1997).
Wang, et al.; "Simultaneous phase and size control of upconversion nanocrystals through lanthanide doping"; Nature; vol. 463, No. 7284, pp. 1061-1065 (Feb. 25, 2010).
Barchet, et al.; "Challenges and opportunities in CNS delivery of therapeutics for neurodegenerative diseases"; Expert Opinion on Drug Delivery; vol. 6, No. 3, pp. 211-225 (Mar. 16, 2009).
Bowers, et al.; "Genetic therapy for the nervous system"; Human Molecular Genetics; vol. 20, No. 1, pp. R28-R41 (2011).
Castagne, et al.; "Rodent Models of Depression: Forced Swim and Tail Suspension Behavioral Despair Tests in Rats and Mice"; Current Protocols in Pharmacology; Supp. 49, Unit 5.8.1-5.8.14 (Jun. 2010).
Friedman, et al.; "Programmed Acute Electrical Stimulation of Ventral Tegmental Area Alleviates Depressive-Like Behavior"; Neuropsychopharmacology; vol. 34, pp. 1057-1066 (2009).
GenBank Accession No. AC096118.6; Rattus norvegicus clone CH230-11 B15, 1-4, 24-25, Working Draft Sequence, 3 unordered pieces. May 10, 2003.
GenBank Accession No. U79717.1; Rattus norvegicus dopamine 02 receptor 1-4, 24-25 gene, promoter region and exon 1. Jan. 31, 1997.
Haim, et al.; "Gene Therapy to the Nervous System"; Stem Cell and Gene-Based Therapy; Section 2, pp. 133-154 (2006).
Pandya, et al.; "Where in the Brain Is Depression?"; Curr. Psychiatry Rep.; vol. 14, pp. 634-642 (2012).
Stonehouse, et al.; "Caffeine Regulates Neuronal Expression of the Dopamine 2 Receptor Gene"; Molecular Pharmacology; vol. 64, No. 6, pp. 1463-1473 (2003).
Ibbini, et al.; "A Field Conjugation Method for Direct Synthesis of Hyperthermia Phased-Array Heating Patterns"; IEEE Transactions on Ultrasonics, Ferroelectrics, and Frequency Control; vol. 36, No. 1, pp. 3-9 (Jan. 1989).
Berlanga, et a.; "Cholinergic Interneurons of the Nucleus Accumbens and Dorsal Striatum are Activated by the Self-Administration of Cocaine"; Neuroscience; vol. 120, pp. 1149-1156 (2003).
Day, et al.; "The Nucleus Accumbens and Pavlovian Reward Learning"; Neuroscientist; vol. 13, No. 2, pp. 148-159 (Apr. 2007).
Knopfel, et al.; "A comprehensive concept of optogenetics"; Progress in Brain Research; vol. 196, pp. 1-28 (2012).
Packer, et al.; "Targeting Neurons and Photons for Optogenetics"; Nature Neuroscience; vol. 16, No. 7, pp. 805-815 (Jul. 2013).

Davidson, et al.; "Viral Vectors for Gene Delivery to the Nervous System"; Nature Reviews Neuroscience; vol. 4, pp. 353-364 (May 2003).
Fanselow, et al.; "Why We Think Plasticity Underlying Pavlovian Fear Conditioning Occurs in the Basolateral Amygdala"; Neuron; vol. 23, pp. 229-232 (Jun. 1999).
Rogers, et al.; "Effects of ventral and dorsal CA1 subregional lesions on trace fear conditioning"; Neurobiology of Learning and Memory; vol. 86, pp. 72-81 (2006).
Chow, et al.; "High-performance genetically targetable optical neural silencing by light-driven proton pumps"; Nature; vol. 463, pp. 98-102 (Jan. 7, 2010).
Gong, et al.; "Enhanced Archaerhodopsin Fluorescent Protein Voltage Indicators"; PLOS One; vol. 8, Issue 6, 10 pages. (Jun. 2013).
Han, et al.; "A high-light sensitivity optical neural silencer: development and application to optogenetic control of non-human primate cortex"; Frontiers in Systems Neuroscience; vol. 5, Article 18, pp. 1-8 (Apr. 2011).
Jones, et al.; "Animal Models of Schizophrenia"; British Journal of Pharmacology; vol. 164, pp. 1162-1194 (2011).
Ferenczi, et al.; "Optogenetic approaches addressing extracellular modulation of neural excitability"; Scientific Reports; vol. 6, 20 pages (Apr. 5, 2016).
Li, et al.; "A Method for Activation of Endogenous Acid-sensing Ion Channel 1a (ASIC1a) in the Nervous System with High Spatial and Temporal Precision"; The Journal of Biological Chemistry; vol. 289, No. 22, pp. 15441-15448 (May 30, 2014).
Shimizu, et al.; "NMDA Receptor-Dependent Synaptic Reinforcement as a Crucial Process for Memory Consolidation"; Science; vol. 290, pp. 1170-1174 (Nov. 10, 2000).
Zeng, et al.; "Activation of acid-sensing ion channels by localized proton transient reveals their role in proton signaling"; Scientific Reports; vol. 5, 14 pages (Sep. 15, 2015).
Zeng, et al.; "Proton production, regulation and pathophysiological roles in the mammalian brain"; Neuroscience Bulletin; vol. 28, No. 1, pp. 1-13 (Feb. 1, 2012).
Definition of Implant; Merriam-Webster Dictionary; retrieved Nov. 7, 2016 (http://www.merriam-webster.com/dictionary/implant).
Definition of integral. Merriam-Webster Dictionary, retrieved on Mar. 20 2017; Retrieved from the internet: <http://www.merriam-webster.com/dictionary/integral>.
Johnson, et al.; "Differential Biodistribution of Adenoviral Vector In Vivo as Monitored by Bioluminescence Imaging and Quantitative Polymerase Chain Reaction"; Human Gene Therapy; vol. 17, pp. 1262-1269 (Dec. 2006).
Schester, et al.; "Biodistribution of adeno-associated virus serotype 9 (AAV9) vector after intrathecal and intravenous delivery in mouse"; Frontiers in Neuroanatomy; vol. 8, Article 42, pp. 1-41 (Jun. 10, 2014).
Abbott, et al.; "Photostimulation of Retrotrapezoid Nucleus Phox2b-Expressing Neurons In Vivo Produces Long-Lasting Activation of Breathing in Rats"; The Journal of Neuroscience; vol. 29, No. 18, pp. 5806-5819 (May 6, 2009).
Alilain, et al.; "Light-Induced Rescue of Breathing after Spinal Cord Injury"; The Journal of Neuroscience; vol. 28, No. 46, pp. 11862-11870 (Nov. 12, 2008).
Cardin, et al.; "Targeted optogenetic stimulation and recording of neurons in vivo using cell-type-specific expression of Channelrhodopsin-2"; Nature Protocols; vol. 5, No. 2, pp. 247-254 (2010).
Caro, et al.; "Engineering of an Artificial Light-Modulated Potassium Channel"; PLoS One; vol. 7, Issue 8, e43766 (Aug. 2012).
Coleman, et al.; "Assessing Anxiety in Nonhuman Primates"; llar Journal; vol. 55, No. 2, pp. 333-346 (2014).
Hagglund, et al.; "Activation of groups of excitatory neurons in the mammalian spinal cord or hindbrain evokes locomotion"; Nature Neuroscience; vol. 13, No. 2, 8 pages (Feb. 2010).
Kleinlogel, et al.; "A gene-fusion strategy for stoichiometric and co-localized expression of light-gated membrane proteins"; Nature Methods; vol. 8, No. 12, pp. 1083-1091 (Dec. 2011).
Kravitz, et al.; "Regulation of parkinsonian motor behaviours by optogenetic control of basal ganglia circuitry"; Nature; vol. 466, No. 622, 8 pages (Jul. 29, 2010).

(56) References Cited

OTHER PUBLICATIONS

Luo, et al.; "Synthetic DNA delivery systems"; Nature Biotechnology; vol. 18, pp. 33-37 (Jan. 2000).
Maestripieri, et al.; "A modest proposal: displacement activities as an indicator of emotions in primates"; Anim. Behav.; vol. 44, pp. 967-979 (1992).
Nelson, et al.; "Non-Human Primates: Model Animals for Developmental Psychopathology"; Neuropsychopharmacology; vol. 34, No. 1, pp. 90-105 (Jan. 2009).
Tomita, et al.; "Visual Properties of Transgenic Rats Harboring the Channelrhodopsin-2 Gene Regulated by the Thy-1.2 Promoter"; PLoS One; vol. 4, No. 11, 13 pages (Nov. 2009).
Uniprot Accession No. P02945, integrated into the database on Jul. 21, 1986.
Lin, et al.; "Study of the Circuitry of Nucleus Accumbens and its Effect on Addiction by Optogenetic Methods: 964"; Neurosurgery; vol. 67, No. 2, pp. 557 (Aug. 2010).
Tsuchida; "Nervous Control of Micturition"; The Japanese Journal of Urology; vol. 80, No. 9, pp. 1257-1277 (1989).
Azizgolshani, et al.; "Reconstituted plant viral capsids can release genes to mammalian cells"; Virology; vol. 441, No. 1, pp. 12-17 (2013).
Racaniello; "How many viruses on Earth?"; Virology Blog; 6 pages; http://www.virology.ws/2013/09/06/how-many-viruses-on-earth/ (Sep. 6, 2013).
Gerits, et al.; "Optogenetically Induced Behavioral and Functional Network Changes in Primates"; Current Biology; vol. 22, pp. 1722-1726 (Sep. 25, 2012).
Han, et al.; "Optogenetics in the nonhuman primate"; Prog. Brain Res.; vol. 196, pp. 215-233 (2012).
Bibel, et al.; "Differentiation of mouse embryonic stem cells into a defined neuronal lineage"; Nature Neuroscience; vol. 7, No. 9, pp. 1033-1009 (Sep. 2004).
Daniel, et al.; "Stress Modulation of Opposing Circuits in the Bed Nucleus of the Stria Terminalis"; Neuropsychopharmacology Reviews; vol. 41, pp. 103-125 (2016).
Hammack, et al.; "The response of neurons in the bed nucleus of the stria terminalis to serotonin Implications for anxiety"; Progress in Neuro-Psychopharmacology & Biological Psychiatry; vol. 33, pp. 1309-1320 (2009).
Knopfel, et al.; "Remote control of cells"; Nature Nanotechnology; vol. 5, pp. 560-561 (Aug. 2010).
Steimer; "The biology of fear- and anxiety-related behaviors"; Dialogues in Clinical Neuroscience; vol. 4, No. 3, pp. 231-249 (Sep. 2002).
Stuber; "Dissecting the neural circuitry of addiction and psychiatric disease with optogenetics"; Neuropsychopharmacology; vol. 35, No. 1, pp. 341-342 (2010).
Gritton, et al.; "Optogenetically-evoked cortical cholinergic transients in mice expressing channelrhodopsin-2 (ChR2) in cholinergic neurons"; Society for Neuroscience Abstract Viewer and Itinery Planner & 40th Annual Meeting of the Society-for-Neuroscience; vol. 40, 2 pages (2010).
Sofuoglu, et al.; "Cholinergic Functioning in Stimulant Addiction: Implications for Medications Development"; CNS Drugs; vol. 23, No. 11, pp. 939-952 (Nov. 1, 2009).
Witten, et al.; "Cholinergic interneurons of the nucleus accumbens control local circuit activity and reward behavior"; Society for Neuroscience Abstract Viewer and Itinerary Planner & 40th Annual Meeting of the Society-for-Neuroscience; vol. 40, 2 pages (2010).
X. Wang et al. "Direct-current Nanogenerator Driven by Ultrasonic Waves." Science 316: 102-105 (Apr. 2007).
K. Hynynen et al. "Clinical applications of focused ultrasound—The brain." Int. J. Hyperthermia 23(2): 193-202 (Mar. 2007).
K. Shibasaki et al. "Effects of body temperature on neural activity in the hippocampus: Regulation of resting membrane potentials by transient receptor potential vanilloid 4." The Journal of Neuroscience 27(7): 1566-1575 (Feb. 2007).
G. Brown et al. "Long-term potentiation induced by Θ frequency stimulation is regulated by a protein phosphate-1-operated gate." The Journal of Neuroscience 20(21) 7880-7887 (Nov. 2000).
E. Guatteo et al. "Temperature sensitivity of dopaminergic neurons of the substantia nigra pars compacta: Involvement of transient receptor potential channels." J. Neurophysiol. 94: 3069-3080 (Jul. 2005).
H. Kato et al. "Present and future status of noninvasive selective deep heating using RF in hyperthermia." Med & Biol. Eng. & Comput 31 Supp: S2-11 (Jul. 1993). Abstract, p. S2 only.
E.A. Gelvich et al. "Contact flexible microstrip applicators (CFMA) in a range from microwaves up to short waves." IEEE Transac. On Biomed. Engineering 49(9): 1015-1023 (Sep. 2002). Abstract only.
Boyden, et al.; "A history of optogenetics: the development of tools for controlling brain circuits with light"; F1000 Biology Reports; vol. 3, No. 11, 12 pages (May 3, 2011).
Knox, et al.; "Heterologous Expression of Limulus Rhodopsin"; The Journal of Biological Chemistry; vol. 278, No. 42, pp. 40493-40502 (Oct. 17, 2003).
Lin, et al.; "Characterization of Engineered Channelrhodopsin Variants with Improved Properties and Kinetics"; Biophysical Journal; vol. 96, No. 5, pp. 1803-1814 (Mar. 2009).
Friedman, et al.; "VTA Dopamine Neuron Bursting is Altered in an Animal Model of Depression and Corrected by Desipramine"; J. Mol. Neurosci.; vol. 34, pp. 201-209 (2008).
Hackmann, et al.; "Static and time-resolved step-scan Fourier transform infrared investigations of the photoreaction of halorhodopsin from Natronobacterium pharaonis: consequences for models of the anion translocation mechanism"; Biophysical Journal; vol. 81, pp. 394-406 (Jul. 2001).
Weiss, et al.; "Galanin: A Significant Role in Depression?"; Annals New York Academy of Sciences; vol. 863, No. 1, pp. 364-382 (1998).
Winter, et al.; "Lesions of dopaminergic neurons in the substantia nigra pars compacta and in the ventral tegmental area enhance depressive-like behavior in rats"; Behavioural Brain Research; vol. 184, pp. 133-141 (2007).

\* cited by examiner

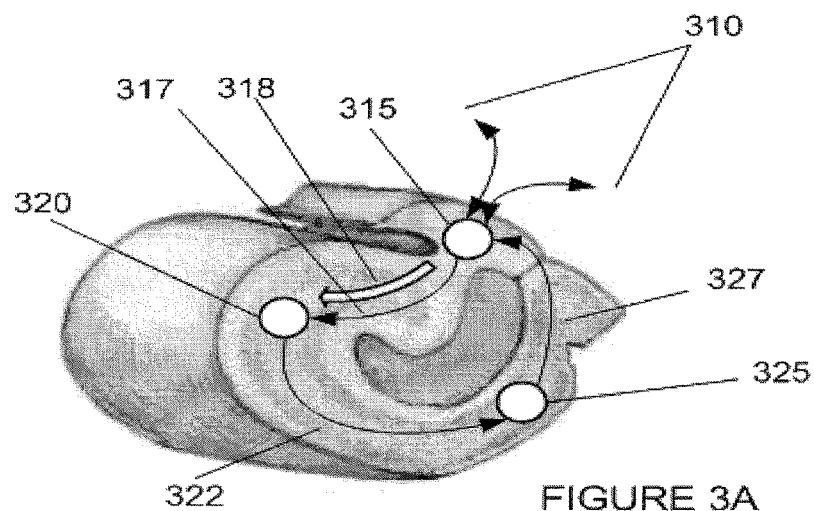
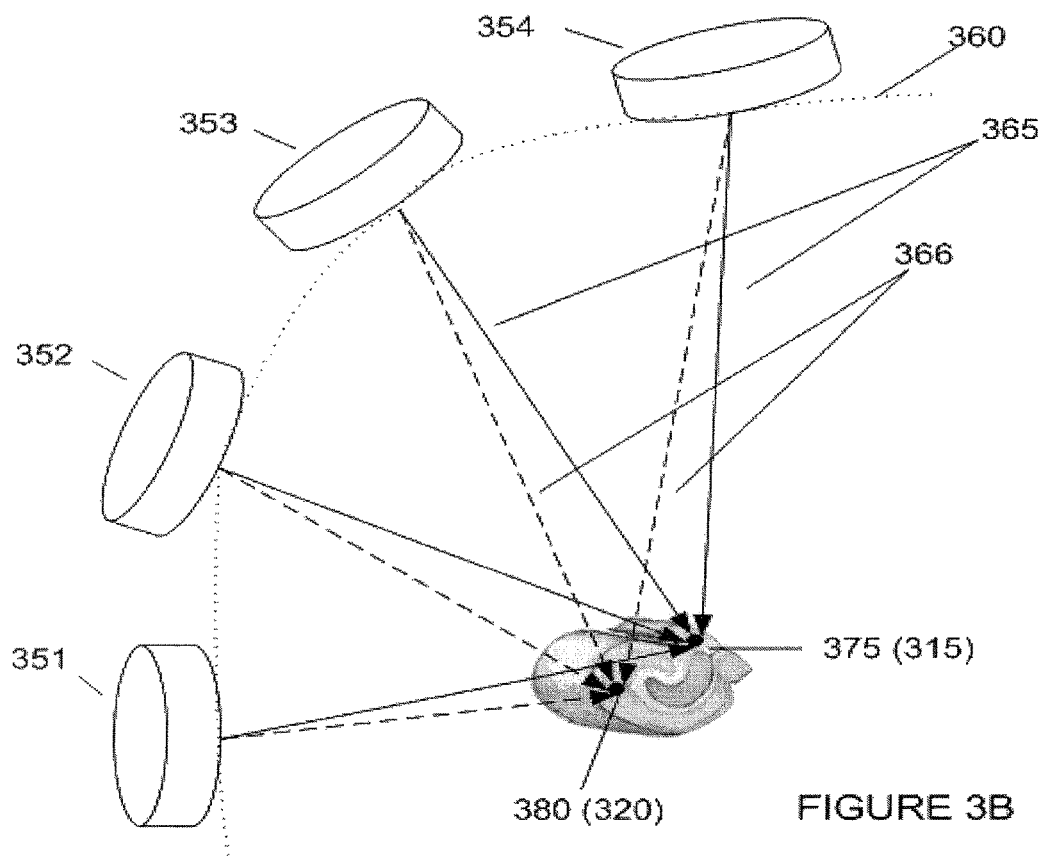

DEVICE AND METHOD FOR ULTRASONIC NEUROMODULATION VIA STEREOTACTIC FRAME BASED TECHNIQUE

RELATED PATENT DOCUMENTS

This is a conversion of U.S. Provisional Patent Application Ser. No. 60/984,225, entitled "Device and Method for Non-Invasive Neuromodulation," and filed on Oct. 31, 2007, to which benefit is claimed under 35 U.S.C. § 119.

FIELD OF THE INVENTION

The present invention relates generally to systems and approaches for stimulation of neural circuits and more particularly to facilitating long-term potentiation or long-term depression between neural circuits.

BACKGROUND

Long-term potentiation (LTP) involves the process of establishing an association between the firing of two cells or groups of cells. For instance, Hebb's rule essentially states that if an axon of cell A is near enough to excite a cell B and repeatedly or persistently takes part in firing cell B, an increase in the strength of the chemical synapse between the cells takes place such that A's efficiency, as one of the cells firing B, is increased. LTP has been shown to last from minutes to several months. Conditions for establishing LTP are favorable when a pre-synaptic neuron and a post-synaptic neuron are both depolarized in a synchronous manner. An opposite effect, long-term depression (LTD), has also been established. LTD is the weakening of a neuronal synapse that lasts from hours to months. In the cerebellar Purkinje cells, LTD results from strong synaptic stimulation. By contrast, in the hippocampus, LTD results from persistent weak synaptic stimulation, or when a pre-synaptic neuron and a postsynaptic neuron discharge in an asynchronous manner. Since the establishment of Hebb's original rule, additional "Hebb's Rules" have been proposed for the prediction of self-organization of neuronal systems, and these rules appear to govern the process by which the brain is effectively sculpted over time in order to master the demands of the environment.

Neurons and other electrically excitable cells (including cardiac cells and some endocrine cells) have spontaneous firing rates: they discharge action potentials at a baseline rate, in the absence of external stimulation or suppression. This spontaneous firing rate is affected by temperature. Generally, the warmer an electrically excitable cell, the faster the spontaneous firing rate, and the colder the cell, the slower the firing rate. When cells become extremely warm, such as in a very high fever, they have a high propensity to fire. At extremes, such an increase in firing rates may manifest as a risk of a febrile seizure.

Neuromodulation is the control of nerve activity, and is usually implemented for the purpose of treating disease. In the strictest sense, neuromodulation may be accomplished with a surgical intervention like cutting an aberrant nerve tract. However, the semi-permanent nature of a surgical procedure leaves little room for later adjustment and optimization. Likewise, it could be asserted that neuromodulation can be accomplished with chemical agents or medications. Chemical agents or medications may be undesirable because, for example, many medications are difficult to deliver to specific anatomy, and because the titration (increasing or decreasing the dose of a medication) is a slow and imprecise way to achieve a desired effect on a specific target. Consequently, the term neuromodulation usually implies the use of energy-delivering devices.

Several categories of device-based neuromodulation methods are known in the art. These include electrical neuromodulation, magnetic neuromodulation and opto-genetic neuromodulation.

Electrical nerve stimulation is well-established. Examples of electrical approaches include transcutaneous electrical nerve stimulation (TENS) units, and the surgically implanted electrodes of deep brain stimulation (DBS). TENS units are used to lessen superficial nerve pain within skin and muscle. Because the device is non-invasive and has a low power output, its use involves little risk. However, the efficacy of TENS is limited to nerve distributions very close to the surface. Additionally, TENS has little focusing ability for targeting with close tolerances. Moreover, its therapeutic use shows a fairly small effective treatment area. DBS is a useful approach for treating conditions including Parkinson's disease, essential tremor, epilepsy, chronic pain, depression and obsessive-compulsive disorder. In the case of Parkinson's disease, a multi-contact electrode may be neurosurgically implanted in the subthalamic nucleus of a patient. Once connected to a pulse generation unit similar to a cardiac pacemaker device, the electrodes may be electrically pulsed at various rates, effectively driving the activity of the neurons immediately adjacent to the electrode contacts, using currents of about 3 amps and voltages between 1 and 10. Subsequently, various configurations of electrode pairs or monopolar configurations may be empirically tested on the patient for effect and tolerability. At a later time, the circuit configuration or pulse parameters may be changed by the physician in charge, usually without the need to physically disturb the implanted electrode. One disadvantage of DBS is that, by definition, it requires a highly invasive and risky neurosurgical implantation procedure. If the site of implantation is later deemed suboptimal, or if the device physically fails, more surgery is required.

Magnetic stimulation involves the discharge of large capacitors into an electrically conductive coil placed external to a patient's brain or body. As electrical current runs through the coil, a magnetic field is induced, which in turn, induces an electric field in nerve membranes and surrounding fluid. This forces nerves to depolarize with each discharge of the capacitors in the machine. Magnetic stimulation, when delivered at rates of 5-20 Hz, tend to be stimulating to nerves that it affects, for some time after the magnetic pulse delivery has stopped. Pulse rates of less than 1 Hz tend to suppress the activity of affected nerves after stimulation has ended. Very fast pulse trains (e.g., 50 Hz), punctuated by absence of pulses 6-9 times per second ("theta rhythm") also tend to suppress the activity of affected neurons. Magnetic neuromodulation, in the form of repetitive transcranial magnetic stimulation, is useful for the treatment of depression, and likely several other neurological and psychiatric conditions. The derived effects may last from minutes to months after the end of magnetic treatment. One limitation of magnetic neuromodulation is the difficulty in achieving tight focus of the effect, since magnetic fields capable of penetrating to useful depth tend to be large in footprint, as dictated by the Biot-Savart Law.

Opto-genetic neuromodulation is a newly discovered approach which has the advantages of being neuron-type specific. Using this approach, light-sensitive ion channels or pumps are genetically transferred to the targeted neurons of the brain to be stimulated. A flashing light from an implanted device provides a signal to these channels or pumps to activate. This leads to either neuronal depolarization, or neuronal hyperpolarization, depending upon the nature of the light-sensitive channel or pump. Opto-genetic approaches lend themselves to both neuronal up-regulation and down-regulation. Disadvantages include the requirement of implanted hardware, and the need for the genetic modification of targeted neurons.

Ultrasound is mechanical vibration at frequencies above the range of human hearing, or above 16 kHz. Most medical uses for ultrasound use frequencies in the range of 1 to 20 MHz. Low to medium intensity ultrasound products are widely used by physicians, nurses, physical therapists, masseurs and athletic trainers. The most common applications are probably warming stiff, swollen or painful joints or muscles in a manner similar to a hot compress, but with better penetration. Many ultrasound products have been commercially available for years, including consumer-grade massage machines. By design, the power on these devices is designed to be too low to warm or otherwise affect structures more than two centimeters or so below the surface. Also, these devices are not capable of tight focus at depth, nor are there means for accurately aiming such devices toward precise structural coordinates within the body. As ultrasound of sufficient strength can cause pain in peripheral nerves with each pulse, it is likely that mechanical perturbations caused by ultrasound can cause nerves to discharge.

SUMMARY OF THE INVENTION

Various aspects of the present invention are directed to addressing the above issues and/or generally advancing technology in the above-discussed contexts and other contexts.

In accordance with one embodiment, the present invention is directed to methods, devices and systems that are used to modify neural transmission patterns between neural structures and/or regions. Consistent herewith, one exemplary method involves directing sound waves toward a first targeted neural structure, controlling characteristics of the sound waves at the first target neural structure with respect to characteristics of sound waves at the second target neural structure, and in response, modifying neural transmission patterns. In a related embodiment, a transducer produces the sound for stimulating the first neural structure and the second neural structure, and an electronically-based control circuit is used to control characteristics of the sound waves as described above to modify the neural transmission patterns between the first and second neural structures.

In accordance with one embodiment, the present invention is directed to methods, devices and systems that are used to modify neural transmission patterns between neural structures and/or regions. Consistent herewith, one exemplary method involves directing stimuli toward a first targeted neural structure, controlling characteristics of the stimulus at the first target neural structure with respect to characteristics of stimulus at the second target neural structure, and in response, modifying neural transmission patterns. In a related embodiment, a transducer produces the stimulus for the first neural structure and the second neural structure, and an electronically-based control circuit is used to control characteristics of the stimulus as described above to modify the neural transmission patterns between the first and second neural structures.

As discussed with the detailed description that follows, more specific embodiments of the present invention concern various levels of detail for controlling the neural-transmission modulation.

The above summary of the present invention is not intended to describe each illustrated embodiment or every implementation of the present invention. The figures in the detailed description that follow more particularly exemplify these embodiments.

BRIEF DESCRIPTION OF THE DRAWINGS

The invention may be more completely understood in consideration of the detailed description of various embodiments of the invention that follows in connection with the accompanying drawings, in which:

FIG. 3A shows a specific application of the present invention in which LTP is facilitated within the "trisynaptic circuit" of the human hippocampus, according to an example embodiment of the present invention;

FIG. 3B shows the use of the present invention, to produce LTP between the entorhinal cortex and the CA3 fields of a human hippocampus, as can be used to augment the encoding of memory, according to an example embodiment of the present invention;

Figure 1:
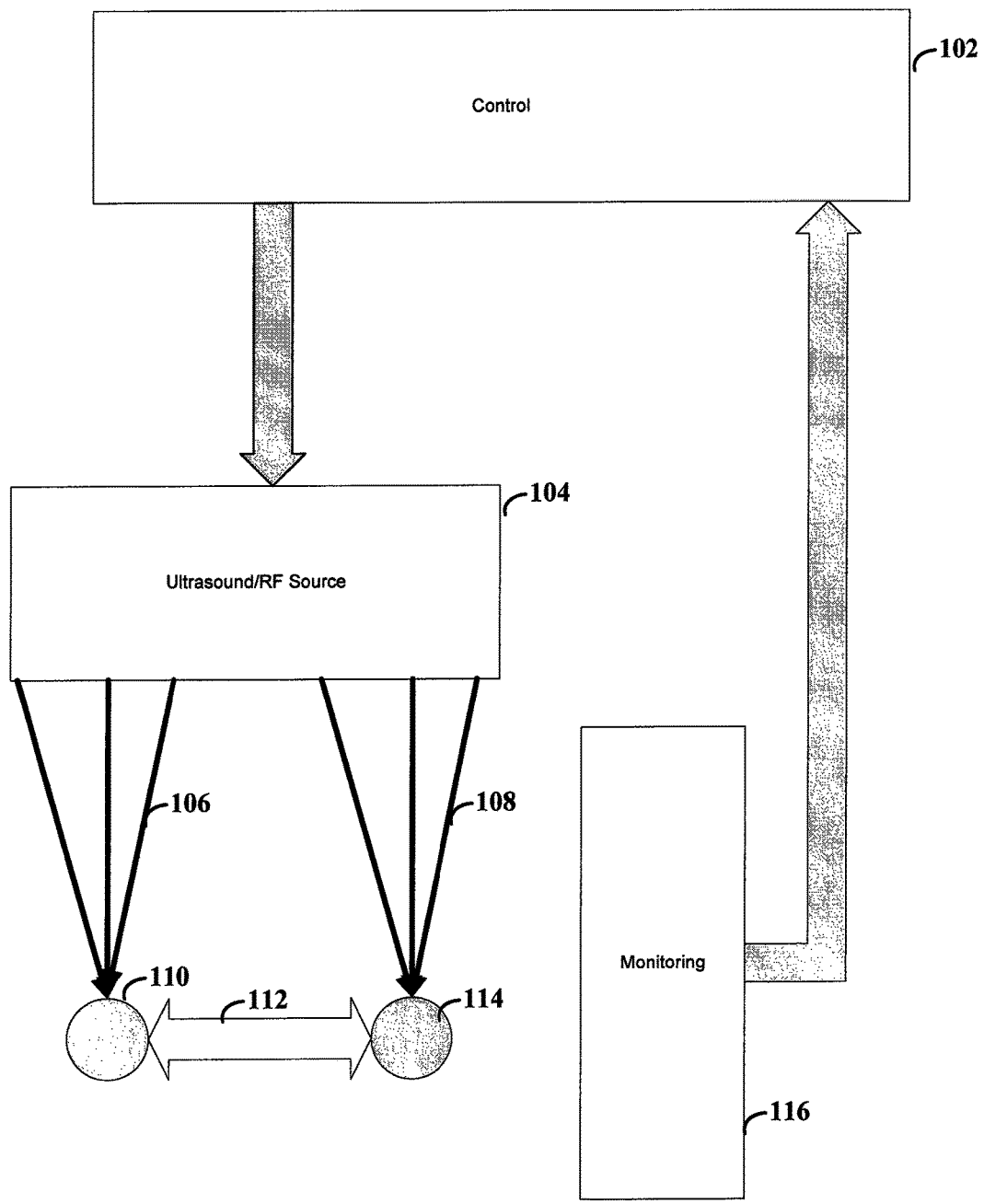
FIG. 1 shows a system for altering neural patterns between two groups of cells, according to an example embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention is believed to be useful for enabling practical application of a variety of LTP and LTD systems, and the invention has been found to be particularly suited for use in systems and methods dealing with generating LTP or LTD effects in neural circuits through the use of sounds waves (which may include high-intensity focused ultrasound), radio frequency (RF) transmissions, electrical current, magnetic fields or ionizing radiation. In the context of this invention, the terms "sound" and "ultrasound" are used interchangeably. For simplicity, while the present invention is not necessarily limited to such applications, various aspects of the invention may be appreciated through a discussion of various examples using this context.

Various embodiments of the present invention are directed toward the use of ultrasound to produce LTP or LTD within a living subject. Sound waves are used to stimulate a first portion of neurons. For LTP, the sound waves are used to concurrently stimulate a second portion of neurons in a synchronous manner. For LTD, the sound waves are used to stimulate a second portion of neurons in an asynchronous manner. Sound waves provide stimulation both in terms of thermal properties and mechanical jarring. While specific embodiments and applications thereof involve sound waves being in the ultrasound frequency range, they need not be so limited. For example, aspects of the present invention can employ frequencies that are outside of the ultrasound frequency range.

In accordance with one embodiment, the present invention is directed to a method for modifying neural transmission patterns between neural structures. The method involves producing and directing sound waves or RF transmissions toward a first targeted neural structure, controlling characteristics of the sound waves or RF transmissions at the first target neural structure with respect to characteristics of sound waves or RF transmissions at the second target neural structure, and thereby modifying neural transmission patterns. In a related embodiment, a transducer produces the sound for stimulating the first neural structure and the second neural structure, and an electronically-based control circuit is used to control characteristics of the sound waves as described above to modify the neural transmission patterns between the first and second neural structures. In another related embodiment, a RF transmitter is used to produce RF transmissions and to focus the transmissions toward a first target neural structure.

In a more specific embodiment, the present invention uses High-intensity Focused Ultrasound (HIFU) as a powerful ultrasound emitter. In connection herewith, ultrasound waves are aimed and focused at a targeted depth geometrically, for example, by using a lens at the emitting end, or by using a curved transducer portion (e.g., a partial sphere). Ultrasound may also be aimed and focused electronically, by coordinating the phase and intensity of individual transducer elements within an array, thereby steering the location of greatest intensity, and even correcting for transmission distortions created, for example by inhomogeneities in the skull. As an ultrasound wave travels through tissue, the mechanical excitation of the tissue generates heat. Thus, the focal point of a HIFU system may be heated substantially in response to the ultrasound. Excessive heat may cause cell damage or even cell death. The threshold for cell death is generally bringing the targeted tissue to 56 degrees Celsius for one second, or 52 degrees Celsius for a longer period of time. Also, tissues held above 43 degrees Celsius for more than an hour or so may have their physiological processes (including cell division) interrupted. Accordingly, to change the firing patterns of targeted neurons, the temperature can be raised to a more moderate temperature above the normal 37 degrees Celsius. In another example, the targeted neurons may be raised to 40-42 degrees Celsius for repeated, brief periods of time, resulting in an increased spontaneous firing rate, and enabling one step of the LTP/LTD induction process.

For further information on the use of such HIFU, and related systems, reference may be made to various literature including, for example, U.S. Pat. No. 4,616,231, filed on Mar. 26, 1984 to Autrey et al. and entitled "Narrow-band beam steering system," U.S. Pat. No. 4,865,042, filed on Aug. 8, 1986 to Umemura et al. and entitled "Ultrasonic irradiation system," U.S. Pat. No. 5,520,188, filed on Nov. 2, 1994 to Hennige et al. and entitled "Annular array transducer," U.S. Pat. No. 7,175,596 filed on Oct. 29, 2001 to Vitek et al. and entitled "System and method for sensing and locating disturbances in an energy path of a focused ultrasound system," U.S. Pat. No. 6,805,129 filed on Oct. 27, 2000 to Pless et al. and entitled "Apparatus and method for ablating tissue," and U.S. Pat. No. 6,506,154 filed on Nov. 28, 2000 to Ezion et al. and entitled "Systems and methods for controlling a phased array focused ultrasound system," each of which is fully incorporated herein by reference. An MRI guided approach to beam aiming with improved phase adjustment focusing techniques incorporates stereotactic capabilities into HIFU. Some of the focused ultrasound systems have shown effectiveness for accurately targeting small lesions within the brain, thermally destroying the targeted tissue, and leaving surrounding tissue unharmed. A few devices allow for the destruction of brain tumors in a non-invasive manner (i.e., through an intact skull).

According to yet another embodiment of the present invention, HIFU is used to stimulate two different areas of the brain. The stimulation of each area is coordinated in order to facilitate the development of either LTP or LTD between the two different areas of the brain. For example, each of the areas can be stimulated in a synchronous fashion to produce LTP. If the stimulation results in an increased rate of depolarization of the neurons, the probability that both areas of the brain will fire at the same time is likewise increased. Moreover, LTP may be developed where the stimulation results in one of the areas generating action potentials more readily in response to stimulus from the other area (e.g., by having a lower depolarization threshold). In order to produce LTD, the areas may be stimulated in an asynchronous fashion to produce an increased probability of the different areas firing independently from one another.

In accordance with the present invention, it has been discovered that not all neurons react in the same fashion to temperature variations. For instance, some neurons increase their firing rate in response to a decrease in temperature and such a response impacts expected efforts in developing LTP or LTD. According to certain embodiments of the present invention, temperature data regarding these neuron-regions are used in developing LTP or LTD between the areas of the brain. In a particular instance, an area of the brain containing neurons that increase their rate of fire due to the stimulation is targeted, and at the same time, another area of the brain containing neurons that decrease their rate of fire due to stimulation is also targeted. This may be particularly useful for facilitating LTD between the targeted areas.

For further information on the use of RF transmitters to elevate temperatures of target cells, reference can be made to Kato H., Ishida T. "*Present and future status of noninvasive selective deep heating using RF in hyperthermia*" Med Biol Eng Comput. 1993 July; 31 Suppl:S2-11 and to Gelvich E A, Mazokhin V N "*Contact flexible microstrip applicators (CFMA) in a range from microwaves up to short waves*" IEEE Trans Biomed Eng. 2002 Sept.; 49(9):1015-23), which are fully incorporated herein by reference. For simplicity, much of the discussion is limited to ultrasound energy; however, the invention is not so limited. For instance, it should be apparent that for many applications the use of RF frequency energy could be used in place of ultrasound energy. Whether by ultrasound, radio frequency energy, or other stimuli, neural effects of the delivered stimulus may be produced by induced temperature alteration, electrical stimulation, or by mechanical perturbation.

FIG. 1 shows a system for altering neural patterns between two groups of cells, according to an example embodiment of the present invention. Ultrasound (or RF) source 104 focuses the ultrasound (or RF) 106, 108 at locations 110 and 114. In some instances, the ultrasound can be focused at only one of the locations, or at one location at a time (e.g., for developing LTD). Control 102 controls the ultrasound produced by ultrasound source 104. In a particular instance, control 102 is responsive to input from monitor device 116. The stimulation from sound (or RF) 106, 108 can be used to effect (e.g., facilitate or frustrate through LTP or LTD) a pathway 112 between locations 110 and 114.

Ultrasound source 104 can be implemented using a number of different techniques and mechanisms. According to one embodiment, ultrasound source 104 is implemented using one single transducer for each of location 110 and 114. Such a transducer acts as a lens to focus the ultrasound waves at a point in space. The control 102 can modify various aspects of the transducer including, but not limited to, direction of focus, distance from the target location, strength of the ultrasound waves or the frequency of the ultrasound waves. Such aspects allow for precise aiming of the focal point of the ultrasound waves. This can be particularly useful for reducing unintended stimulation of cells while increasing stimulation at the target location. In some instances, the transducers can be aimed using piezoelectric devices. Piezoelectric devices allow for minute movements of the transducers in response to electrical signals.

According to another embodiment, ultrasound source 104 is implemented using an array of transducers. In one instance, the array can be implemented as one or more two-dimensional arrays of transducers. In another instance, the array can be implemented using a three-dimensional array, such as an array placed upon the skull of a patient. Similar to the single transducer implementation, the control 102 can modify various aspects of the transducers. In one instance, the transducers are similar to those used by the single transducer implementation in that they function to focus the ultrasound waves at a point in space. The array provides a summation of the effects from the transducers in order to further focus ultrasound waves. In one instance, each transducer can be individually calibrated so as to focus the ultrasound waves at the desired location. Control 102 can then alter the phase of each transducer such that the ultrasound waves provide constructive interference rather than destructive interference so as to increase the effectiveness of the delivered ultrasound energy. In another instance, the individual transducers of the array of transducers offer little directional or focusing effect when used in isolation. Control 102 modifies the aspects of the ultrasound waves of the array so as to effectively focus the ultrasound waves at the target location.

In various embodiments of the invention, control 102 can use monitoring device 116 to determine the appropriate aspects for the transducer(s). For instance, monitoring device 116 may be implemented using, for example, the ExAblate® system (InSightec Ltd. Haifa, Israel). The input from such device provides a determination as to the effectiveness of the current settings of transducer(s).

Although not shown, various embodiments of the invention may also be implemented using devices or methods to effectively determine the target location. These implementations can be particularly useful for providing improved accuracy of the ultrasound waves by precisely targeting the desired location. An example of a possible targeting method and system includes the targeting system of the ExAblate® (InSightec Ltd. Haifa, Israel). Alternatively, the system may be targeted by registering the ultrasound probes to a commercially available user-configurable tool or "universal tool" on a neuronavigation system such as the StealthStation by the Surgical Navigation Technologies division of Medtronic, Inc. (Minneapolis, Minn.). Targeting may also be achieved by affixing ultrasonic transducers to a stereotactic frame, and moving them into correct targeting position via frame-based techniques, such as those used for neurosurgery.

The display of the effect at the target may be augmented with a registration and display of calculated or measured temperature at the target site, or a measurement or calculation of neuronal activity at the target site. Temperature displays, e.g., obtained from thermal tomography systems, may be derived from measured values or from projected/calculated values. Examples of measurements and display of neuronal activity include multichannel EEG (for example Brain Electrical Activity Monitoring or BEAM) or mangeto-encephalography (MEG).

Figure 2A:
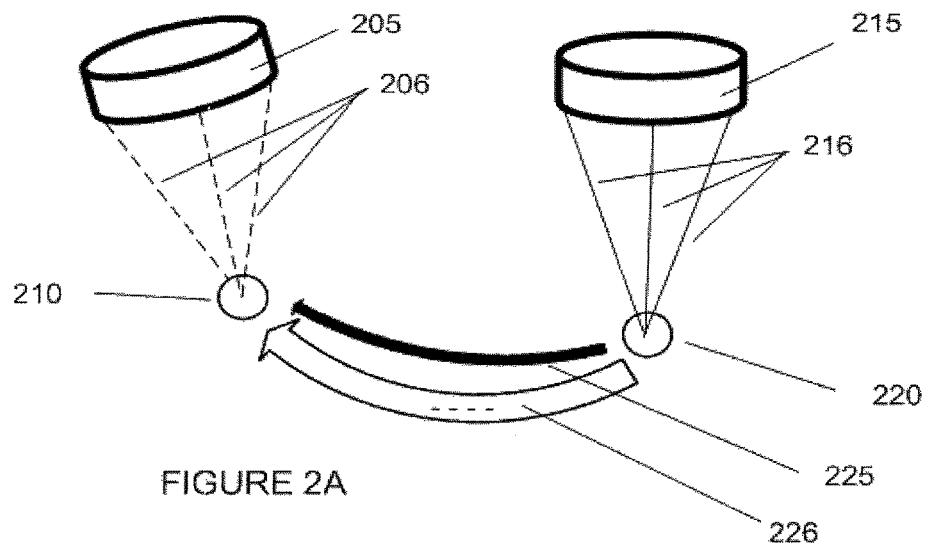
FIG. 2A shows the use of two focused-beam ultrasound transducers physiologically suppressing the connection between two regions, according to an example embodiment of the present invention.

FIG. 2A shows the use of two focused-beam ultrasound transducers physiologically suppressing the connection between the two regions by virtue of a mechanism such as long-term depression (LTD). An ultrasound transducer 205 delivers ultrasound energy to neural target 210 via ultrasound vectors 206. Ultrasound transducer 215 also delivers energy to neural target 220 via ultrasound vectors 216. Neural target 220 is connected to neural target 210 via neuronal tract 225. As target 220 and target 210 are stimulated in a slow-pulse rate, asynchronous fashion, long-term depression (LTD) process 226 is initiated within tract 225. The presence of LTD makes tract 225 less excitable than it would be under normal circumstances. In many instances, such a depressed excitability level is maintained for a period of weeks. Conversely, LTP may be induced with these focused-beam transducers by changing to a more rapid, regular and strong pulse pattern.

Figure 2B:
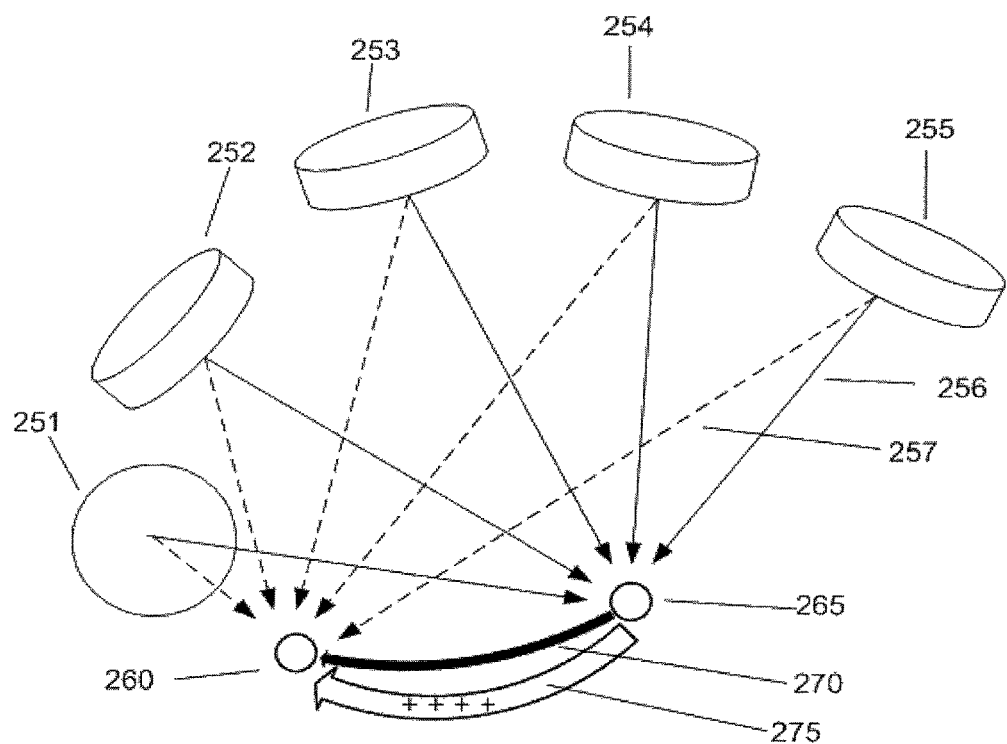
FIG. 2B shows the use of an electronically focused ultrasound transducer array to physiologically augment the connection between two regions, according to an example embodiment of the present invention.

FIG. 2B shows the use of an electronically focused ultrasound transducer array to physiologically augment the connection between the two regions by virtue of a mechanism such as LTP, according to an example embodiment of the present invention. Neural target 265 is connected via neural tract 270, to neural target 260. Ultrasound transducers 251, 252, 253, 254 and 255 contribute to the total energy delivered to both neural target 260 (via dashed lines 257) and to neural target 265 (via solid lines 256), by virtue of electronic focusing techniques. Neural target 265 and target 260 are stimulated in a rapid and regular fashion to initiate an LTP process 275 within tract 270. In a specific example, the target areas are regularly pulsed at a rate of 1 Hz or more, or mildly heated at the same time thereby increasing the neuronal firing rate in tract 270. This allows for the creating of LTP, or enduring enhancement of the stimulation, along tract 270. The presence of LTP increases the excitability level of tract 270 relative to normal circumstances. In certain instances, such an increased excitability level can be maintained for a period of weeks. Conversely, LTD may also be produced with this electronically focused transducer array by changing to a weaker, slow, asynchronous pattern of pulsing.

FIG. 3A shows a specific application of the present invention in which LTP is facilitated within the "trisynaptic circuit" of the human hippocampus according to an example embodiment of the present invention. In the trisynaptic circuit, cerebral cortical regions (not shown) have connections 310 to entorhinal cortex 315. Entorhinal cortex 315 is connected to CA3 field 320 via connection 317. CA3 field 320 relays signals to CA1 field 325, via connection 322. CA1 field 325 relays back to entorhinal cortex 315 via connection 327. Finally, entorhinal cortex 315 relays data back to cerebral cortex regions via connections 310. When rapid and strong stimulations are applied to entorhinal cortex 315, long-term potentiation (318) is established along connection 317 between entorhinal cortex 315 and CA3 field 320. Moreover, it is believed that the application of stimulation to both entorhinal cortex 315 and CA3 field 320 may improve the speed at which the LTP effect is created and also improve the length that the LTP effect is sustained.

FIG. 3B shows the use of the present invention, (in a form similar to that shown in FIG. 2B) to produce LTP between the entorhinal cortex and the CA3 fields of a human hippocampus, as can be used to augment the encoding of memory. Specifically, entorhinal cortex 375 is connected to CA3 field 380 (same as 315 and 320, respectively, in FIG. 3A). Ultrasound transducers 351, 352, 353 and 354 are arranged around a patient's scalp 360 in order to stimulate both the CA3 field 380 (via dashed lines 366) and the entorhinal cortex 375 (via solid lines 365), by virtue of electronic focusing techniques. By stimulating the entorhinal cortex 375 and CA3 field 380 in a rapid and regular fashion, a LTP process 318 is initiated within connecting tract 317 as shown in FIG. 3A.

Figure 4A:
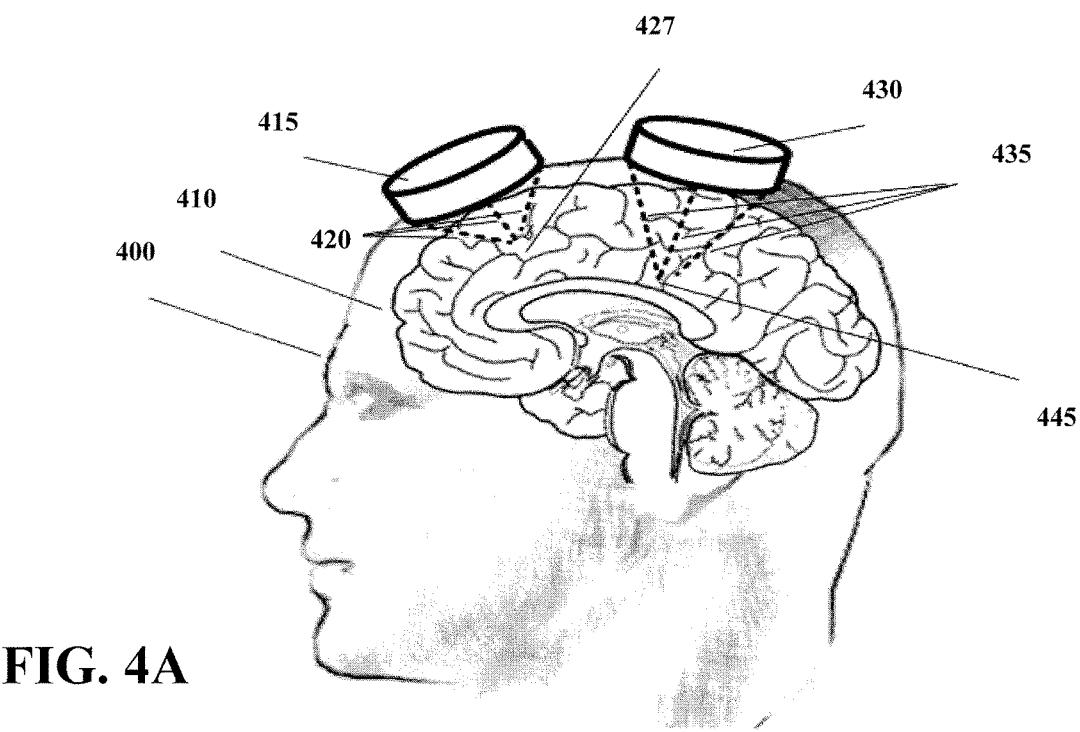
FIG. 4A shows the use of two focused-beam ultrasound transducers, each focused upon a different, but connected neural target, according to an example embodiment of the present invention.

FIG. 4A shows the use of two focused-beam ultrasound transducers, each focused upon a different, but connected neural target, according to an example embodiment of the present invention. Transducer 415 and 430 each focuses ultrasound waves 420 and 435, respectively, to specific points within the brain 410 of patient 400. More specifically, transducer 415 focuses the ultrasound to target point 427 and transducer 430 focuses the ultrasound at target point 445.

The focus points of the transducers can be controlled by modifying direction of the ultrasound waves 420 and 435. For instance, transducers having different curvatures may be used to provide different depths of convergence. Likewise, the transducer's position on the skull and distance therefrom can be modified to set the convergence point within the brain 410. The direction of the ultrasound waves can be modified by controlling the angle of the transducers 415 and 430 relative to brain 410. This can be accomplished using a variety of approaches. One such approach involves setting the angle using a structure that supports the transducers and allows for adjustment of the angle. The patient's skull can then be immobilized relative to the structure. Another approach involves attaching the transducers directly to the patient's scalp, skull, or by surgically implanting them upon or within the brain itself. The angle may be set accordingly.

Figure 4B:
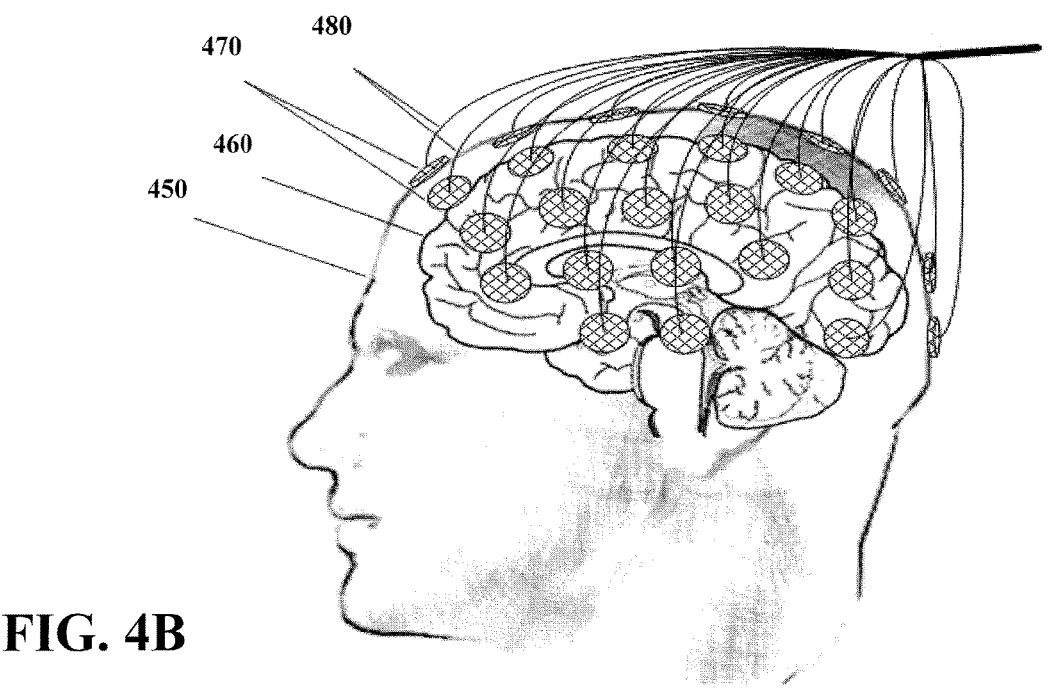
FIG. 4B shows an array of multiple small ultrasound transducers which may be electronically directed at one or more target regions within a patient's brain via a coordinated phase and power adjustment, also according to the present invention.

FIG. 4B shows the use of an array of multiple small ultrasound transducers which may be electronically focused upon one or more targets within a patient's brain by virtue of a coordinated phase and power adjustment to the transducers in the array, according to an example embodiment of the present invention. An array of transducers 470 is attached to patient 450 for the purpose of stimulating brain 460. Individual control of the transducers is provided through communication connections 480, which are shown as wires in FIG. 4B. Examples of suitable communications connections include electrical wires, wireless transmissions and optical fibers. In some instances, power is delivered to transducers 470 through the same (or similar) connections.

According to one embodiment of the invention, the power, frequency and phase of the transducers can be modified to pinpoint the desired target locations. The delay from the time that the ultrasound wave is first transmitted to the time the ultrasound wave arrives at the target location may vary from transducer to transducer (e.g., due to differences in the location and orientation of the transducers). For instance, the distance and type of tissue can directly affect the propagation time of the ultrasound wave. A control device can compensate for differences between the transducers to ensure that the ultrasound waves add to the power of the stimulation at the desired location. In some instances, one or more of the transducers may not provide any appreciable addition to the amount of stimulation at the target location. In other instances, one or more of the transducers may create undesirable effects, such as stimulation of areas other than the target locations. For such instances, the transducer power may be reduced or removed completely. The ineffectiveness of a few of such transducers may be offset by increasing the power of the other transducers or by providing a sufficiently large array of transducers. Other variations are possible including grouping control of a number of transducers together rather than individually controlling each transducer. This may be particularly useful for reducing the complexity of the communications and the complexity of various control parameters.

Once the selected phase, frequency and other constraints are set, the transducers can be used to stimulate two different target areas in a synchronous or asynchronous manner to produce LTP or LTD, respectively, between the different target areas. The invention need not be limited to only two target areas. For instance, three or more areas of the brain may be stimulated for the purposes of facilitating LTP or LTD therebetween. In another instance, a number of different target areas may be sequentially stimulated to produce an LTP communication pathway of related target areas. Similarly, a sequence of different target areas may be stimulated to disrupt a communication pathway by producing LTD between the sequential target areas. Various combinations thereof are also possible.

In conjunction with a specific embodiment of the present invention, the thermal properties of sound waves are supplemented with electrical impulses generated by implanted devices that respond to mechanical motion produced by the sound waves. For instance a device, implanted surgically in proximity to a group of neurons that one wishes to affect, electrically stimulates those neurons when in receipt of sound waves.

In one such embodiment, implanted piezoelectric antennas are surgically implanted adjacent to the neural structure that is the target of the modulation. Such antennae produce electrical current via the piezoelectric effect of an implanted piezoelectric generator, which is rapidly moved back and forth by externally applied ultrasound. The electric current from the piezoelectric generator serves to stimulate neurons electrically, in response to the externally applied ultrasonic waves. All other principles of synchrony and asynchrony as they apply to the induction of LTP and LTD, respectively, still hold under this paradigm. The implanted ultrasound-to-electrical current conversion device serves to enhance the same processes as previously described herein. For further information regarding implanted piezoelectric antennas, reference may be made to recent publications including, for example, Wang X, Song J, Liu J, Wang Z L, in Direct-current Nanogenerator Driven By Ultrasonic Waves, Science, 2007, Apr. 6-316(5821):102-5, which is fully incorporated herein by reference.

In another embodiment of the present invention, such implantable devices can be implemented as the primary source of stimulation (e.g., with minimal thermal heating).

The various embodiments described above are provided by way of illustration only and should not be construed to limit the invention. Based on the above discussion and illustrations, those skilled in the art will readily recognize that various modifications and changes may be made to the present invention without strictly following the exemplary embodiments and applications illustrated and described herein. For instance, such changes may include variations in the duration and frequency of the stimulation between target areas. Such modifications and changes do not depart from the true spirit and scope of the present invention, which is set forth in the following claims.

What is claimed is:

1. A system comprising:
a transducer array comprising:
   a first transducer configured and arranged to direct a first focused ultrasound stimulus to a first target neural structure in a brain of a subject; and
   a second transducer configured and arranged to direct a second focused ultrasound stimulus to a second target neural structure in the brain, wherein the first and second transducers are arranged at different positions around a scalp of the subject,
the targeting of the neural structures are configured to be achieved by affixing the first and second ultrasonic transducers to a stereotactic frame,
wherein the first and second target neural structures are different target neural structures in the brain with a neural pathway that connects the first target neural structure with the second target neural structure, wherein the first target neural structure comprises a neuron pre-synaptic to a neuron in the second target neural structure, and wherein the first and second focused ultrasound stimuli are non-destructive to functional responsiveness of the first and second target neural structures; and
a control circuit,
wherein the control circuit is configured and arranged to electronically direct the first focused ultrasound stimulus and the second focused ultrasound stimulus to the first target neural structure and the second target neural structure, respectively, wherein the first and second transducers are configured to be moved into correct targeting position via frame-based techniques, and control the transducer array, to concurrently alter one or more characteristics of sound waves at the first target neural structure with respect to characteristics of sound waves at the second target neural structure in a synchronous or asynchronous manner.

2. The system of claim 1, wherein modifying the neural transmission patterns comprises one of long-term potentiation and long-term depression of the neural transmission patterns.

3. The system of claim 1, wherein the sound waves at the first target neural structure raise the temperature of the first target neural structure so as to affect a firing rate of neurons in the first target neural structure.

4. The system of claim 1, wherein the transducer arrangement includes a plurality of transducers that are each configured and arranged to be controlled by the control circuit.

5. A method comprising:
producing sound waves using a transducer array comprising:
   a first transducer configured to emit a first focused ultrasound stimulus; and
   a second transducer configured to emit a second focused ultrasound stimulus, wherein the first and second transducers are arranged at different positions around a scalp of the subject;
directing the first focused ultrasound stimulus to a first target neural structure in the brain of a subject;
the targeting of the neural structures are achieved by affixing the first and second ultrasonic transducers to a stereotactic frame,
directing the second focused ultrasound stimulus to a second target neural structure in the brain, wherein the first and second target neural structures are different target neural structures in the brain with a neural pathway that connects the first target neural structure with the second target neural structure, wherein the first target neural structure comprises a neuron pre-synaptic to a neuron in the second target neural structure;
electronically directing the first focused ultrasound stimulus and the second focused ultrasound stimulus to the first target neural structure and the second target neural structure, respectively; and
controlling the transducer array to alter one or more characteristics of sound waves at the first target neural structure with respect to characteristics of the sound waves at the second target neural structure, where the first and second transducers are moved into correct targeting position via frame-based techniques, to stimulate the first target neural structure with the first focused ultrasound stimulus while concurrently stimulating the second target neural structure with the second focused ultrasound stimulus, in a synchronous or asynchronous manner, thereby non-destructively modifying neural transmission patterns along the neural pathway.

6. A device for neuromodulation, the device comprising:
an array of ultrasound energy emitters comprising:
   a first energy emitter configured and arranged to emit a first ultrasound energy that is focused to a first focal point in a brain of a subject; and
   a second energy emitter configured and arranged to emit a second ultrasound energy that is focused to a second focal point in the brain, wherein the first and second energy emitters are arranged at different positions around a scalp of the subject;
the targeting of the first and second focal points are configured to be achieved by affixing the first and second energy emitter to a stereotactic frame,
a first control circuit configured and arranged to register the first and second focal points with two different locations in space in the brain at which the first and second focal points are desired, wherein the locations in space comprise a first target neural structure and a second target neural structure, wherein the first and second target neural structures are different target neural structures in the brain with a neural pathway that connects the first target neural structure with the second target neural structure, wherein the first target neural structure comprises a neuron pre-synaptic to a neuron in the second target neural structure, and wherein the first and second focused emitted energies are non-destructive to functional responsiveness of the first and second target neural structures; and
a second control circuit configured and arranged to electronically direct the first focused ultrasound energy and the second focused ultrasound energy to the first target neural structure and the second target neural structure, respectively, wherein the first and second energy emitter are configured to be moved into correct targeting position via frame-based techniques, and control the array of energy emitters to direct the registered focal points of the emitted energies toward the locations in space, and to non-destructively alter a pattern of functional responsiveness of a plurality of cells at the locations in space, wherein the array of energy emitters stimulates the first target neural structure with the first focused ultrasound energy and concurrently stimulates the second target neural structure with the second focused ultrasound energy, in a synchronous or asynchronous manner.

7. The device of claim 6, further including a secondary group of one or more energy emitters, wherein each of the first and second target neural structures is stimulated by one of the energy emitters.

8. The device of claim 6, wherein the responsiveness between the first target neural structure and the second target neural structure is moderated by long-term potentiation (LTP).

9. The device of claim 6, wherein the responsiveness between the first target neural structure and the second target neural structure is moderated by long-term depression (LTD).

10. The device of claim 6, wherein the energy heats the first target neural structure thereby changing a spontaneous firing rate of the first target neural structure.

11. The device of claim 6, wherein the pattern of functional responsiveness in the plurality of cells is altered due to mechanical perturbations of a cell from the emitted energy.

12. The device of claim 6, wherein the energy is focused using one of a lens and a curved transducer portion.

13. A system comprising:
a transducer array comprising:
a first transducer configured and arranged to direct a first wirelessly transmitted ultrasound stimulus to a first target neural structure in a brain of a subject; and
a second transducer configured and arranged to direct a second wirelessly transmitted ultrasound stimulus to a second target neural structure in the brain, wherein the first and second transducers are arranged at different positions around a scalp of the subject,
the targeting of the neural structures are configured to be achieved by affixing the first and second ultrasonic transducers to a stereotactic frame,
wherein the first and second target neural structures are different target neural structures in the brain with a neural pathway that connects the first target neural structure with the second target neural structure, wherein the first target neural structure comprises a neuron pre-synaptic to a neuron in the second target neural structure, and wherein the first and second wirelessly transmitted ultrasound stimuli are non-destructive to functional responsiveness of the first and second target neural structures; and
a control circuit,
wherein the control circuit is configured and arranged to electronically direct the first wirelessly transmitted ultrasound stimulus and the second wirelessly transmitted ultrasound stimulus to the first target neural structure and the second target neural structure, respectively, wherein the first and second transducers are configured to be moved into correct targeting position via frame-based techniques, and control the transducer array, to concurrently alter one or more characteristics of the first stimulus at the first target neural structure with respect to characteristics of the second stimulus at the second target neural structure in a synchronous or asynchronous manner.

14. A method comprising:
targeting, using a first transducer, a first set of sound waves at a first target neural structure in a brain of a subject, the first target neural structure having a first baseline firing rate;
targeting, using a second transducer, a second set of sound waves at a second target neural structure in the brain, the second target neural structure having a second baseline firing rate, wherein the first and second transducers are arranged at different positions around a scalp of the subject,
the targeting of the neural structures are achieved by affixing the first and second ultrasonic transducers to a stereotactic frame,
wherein the first and second target neural structures are different target neural structures in the brain with a neural pathway that connects the first target neural structure with the second target neural structure, wherein the first target neural structure comprises a neuron pre-synaptic to a neuron in the second target neural structure;
electronically directing the first set of sound waves and the second set of sound waves to the first target neural structure and the second target neural structure, respectively; and
controlling the first and second transducers to alter an intensity of the first and second sets of sound waves to stimulate the first target neural structure with a first focused ultrasound stimulus while concurrently stimulating the second target neural structure with a second focused ultrasound stimulus, in a synchronous or asynchronous manner, where the first and second transducers are moved into correct targeting position via frame-based techniques, to modify the baseline firing rates of the first and second neural structures, respectively,
wherein the controlling comprises timing of the modified baseline firing rate of the first target neural structure relative to the modified baseline firing rate of the second target neural structure in response to a desired change in an association, through the neural pathway, of firing between the first and second target neural structures.

15. The method of claim 14, wherein the desired change includes long-term-potentiation between the first and second target neural structures.

16. The method of claim 14, wherein the desired change includes long-term depression between the first and second target neural structures.

17. The method of claim 14, wherein the timing of the modified baseline firing rates of the first and second neural structures relative to each other includes simultaneous stimulation of both the first and second target neural structures in a periodic fashion at a rate of at least 1 Hz.

18. The method of claim 14, wherein the first neural structure includes neurons in the entorhinal cortex and the second target neural structure includes neurons in the CA3 field.

19. The method of claim 14, wherein the intensity of the first and second sets of sound waves is altered in a manner sufficient to raise the temperature of the first and second target neural structures, respectively, while maintaining the temperature below 42 degrees Celsius.

20. A system comprising:
a transducer array comprising a first transducer producing sound and stimulating a first target neural structure using a first focused ultrasound stimulus concurrently with a second transducer producing sound and stimulating a second target neural structure using a second focused ultrasound stimulus in a brain of a subject, wherein the first and second transducers are arranged at different positions around a scalp of the subject, the targeting of the first and second neural structures are configured to be achieved by affixing the transducer arrays to a stereotactic frame, wherein the first and second target neural structures are different target neural structures in the brain with a neural pathway that connects the first target neural structure with the second target neural structure, wherein the first target neural structure comprises a neuron pre-synaptic to a neuron in the second target neural structure, and wherein the first and second focused ultrasound stimuli are non-destructive to functional responsiveness of the first and second target neural structures;

a control circuit, wherein the control circuit electronically directs the first focused ultrasound stimulus and the second focused ultrasound stimulus to the first target neural structure and the second target neural structure, respectively, wherein the transducer arrays are configured to be moved into correct targeting position via frame-based techniques, and controls the transducer array to alter one or more characteristics of sound waves at the first target neural structure with respect to characteristics of the sound waves at the second target neural structure in a synchronous or asynchronous manner, and wherein synchronous stimulation of the first and second target neural structures induces long-term potentiation, and asynchronous stimulation induces long-term depression along the neural pathway.

21. The system of claim 20, wherein the sound waves at the first target neural structure sufficiently raise the temperature of the first target neural structure so as to affect a firing rate of neurons in the first target neural structure.

22. A device for neuromodulation, the device comprising:
an array of energy emitters comprising:
a first energy emitter that emits a first ultrasound energy that is focused to a first focal point in a brain of a subject; and
a second energy emitter that emits a second ultrasound energy that is focused to a second focal point in the brain, wherein the first and second energy emitters are arranged at different positions around a scalp of the subject;
targeting of the first and second focal points are configured to be achieved by affixing the first and second energy emitter to a stereotactic frame,
a first control circuit that registers the first and second focal points with two different locations in space in the brain at which the first and second focal points are desired, wherein the locations in space comprise a first target neural structure and a second target neural structure, wherein the first and second target neural structures are different target neural structures in the brain with a neural pathway that connects the first target neural structure with the second target neural structure, wherein the first target neural structure comprises a neuron pre-synaptic to a neuron in the second target neural structure; and
a second control circuit that electronically directs the first focused ultrasound energy and the second focused ultrasound energy to the first target neural structure and the second target neural structure, respectively, wherein the first and second energy emitter are configured to be moved into correct targeting position via frame-based techniques, and controls the array of energy emitters to direct the focal points of the emitted energies toward the locations in space to non-destructively alter a pattern of functional responsiveness of neuronal cells at the location in space by stimulating the first target neural structure with a first focused ultrasound stimulus while concurrently stimulating the second target neural structure with a second focused ultrasound stimulus in a synchronous or asynchronous manner for a first time period to change responsiveness between two groups of neuronal cells for a second period of time that is substantially longer than the first period of time,
wherein the responsiveness between the two groups of neuronal cells is moderated by long-term potentiation (LTP) or by long-term depression (LTD).

23. The system of claim 13, wherein the first and second target neural structures comprise two separate groups of neuronal cells in the brain, and
wherein modifying the neural transmission patterns comprises long-term potentiation or long-term depression of the neural transmission patterns.

24. The method of claim 5, wherein the one or more characteristics comprise one or more of a strength, frequency, and phase of the sound waves.

25. The method of claim 24, wherein the controlling comprises altering the phase of the sound waves to: i) synchronously stimulate the first and second target neural structures to induce LTP in the neural pathway; or ii) asynchronously stimulate the first and second target neural structures to induce LDP in the neural pathway.

26. The system of claim 1, wherein the first and second target neural structures comprise regions of the hippocampus.

27. The system of claim 26, wherein the first target neural structure comprises an entorhinal cortex of the hippocampus, and the second target neural structure comprises a CA3 field of the hippocampus.

* * * * *